United States Patent
Palazzotto et al.

(10) Patent No.: US 10,228,344 B2
(45) Date of Patent: Mar. 12, 2019

(54) SENSOR ELEMENT, METHOD OF MAKING THE SAME, AND SENSOR DEVICE INCLUDING THE SAME

(75) Inventors: Michael C. Palazzotto, Woodbury, MN (US); Stefan H. Gryska, Woodbury, MN (US); Paul F. Baude, Maplewood, MN (US); Myungchan Kang, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 167 days.

(21) Appl. No.: 13/825,660

(22) PCT Filed: Sep. 7, 2011

(86) PCT No.: PCT/US2011/050609
§ 371 (c)(1),
(2), (4) Date: Mar. 22, 2013

(87) PCT Pub. No.: WO2012/050686
PCT Pub. Date: Apr. 19, 2012

(65) Prior Publication Data
US 2013/0229194 A1    Sep. 5, 2013

Related U.S. Application Data

(60) Provisional application No. 61/388,146, filed on Sep. 30, 2010.

(51) Int. Cl.
*G01N 27/416* (2006.01)
*G01N 27/12* (2006.01)

(52) U.S. Cl.
CPC ......... *G01N 27/416* (2013.01); *G01N 27/128* (2013.01)

(58) Field of Classification Search
CPC .................. G01N 2027/222; G01N 27/227
See application file for complete search history.

(56) References Cited

U.S. PATENT DOCUMENTS

| | | | | |
|---|---|---|---|---|
| 5,143,696 A | * | 9/1992 | Haas | G01N 27/225 324/663 |
| 6,634,212 B2 | * | 10/2003 | Moos | G01N 27/226 73/23.2 |

(Continued)

FOREIGN PATENT DOCUMENTS

| JP | H02-012047 | 3/1990 |
|---|---|---|
| JP | H05-312754 | 11/1993 |

(Continued)

OTHER PUBLICATIONS

Adams, "Introduction to Capacitors", CapSite 2009, Release 5.0, Site Copyright 1999-2010, Date of last change Sep. 14, 2009, [retrieved from the Internet on May 22, 2013], URL:http://my.execpc.com/~endld, pp. 7.

(Continued)

*Primary Examiner* — Huy Q Phan
*Assistant Examiner* — Adam Clarke
(74) *Attorney, Agent, or Firm* — Bradford B. Wright; Yufeng Dong

(57) ABSTRACT

A sensor element includes a first conductive electrode having a first conductive member electrically coupled thereto; an absorptive dielectric layer comprising a polymer of intrinsic microporosity; and a second conductive electrode having a second conductive member electrically coupled thereto. The second conductive electrode comprises at least one noble metal, has a thickness of from 4 to 10 nanometers and is permeable to at least one organic vapor. The absorptive dielectric layer is at least partially disposed between the first conductive electrode and the second conductive elec- (Continued)

trode. A method of making the sensor element, and sensor device containing it, are also disclosed.

22 Claims, 4 Drawing Sheets

(56) References Cited

U.S. PATENT DOCUMENTS

| | | | |
|---|---|---|---|
| 6,673,533 B1* | 1/2004 | Wohlstadter | B01L 3/5027 204/400 |
| 7,449,146 B2 | 11/2008 | Rakow | |
| 7,556,774 B2 | 7/2009 | Rakow | |
| 7,767,143 B2 | 8/2010 | Wendland | |
| 7,906,223 B2 | 3/2011 | Rakow | |
| 8,378,694 B2 | 2/2013 | David | |
| 8,409,511 B2 | 4/2013 | Thomas | |
| 2002/0142478 A1* | 10/2002 | Wado | G01N 27/124 436/151 |
| 2003/0109056 A1* | 6/2003 | Vossmeyer | G01N 21/77 436/169 |
| 2004/0128823 A1 | 7/2004 | Mole | |
| 2004/0184948 A1 | 9/2004 | Rakow | |
| 2004/0192072 A1* | 9/2004 | Snow | B82Y 10/00 438/800 |
| 2005/0045493 A1* | 3/2005 | Mahurin et al. | 205/775 |
| 2006/0032742 A1* | 2/2006 | Babes-Dornea et al. | 204/400 |
| 2006/0237310 A1* | 10/2006 | Patel et al. | 204/400 |
| 2006/0246273 A1 | 11/2006 | McKeown | |
| 2006/0249402 A1* | 11/2006 | Snow | B82Y 15/00 205/777 |
| 2007/0292957 A1 | 12/2007 | Chua | |
| 2008/0076781 A1 | 3/2008 | Shaw | |
| 2009/0009756 A1 | 1/2009 | Yamamichi et al. | |
| 2010/0006774 A1* | 1/2010 | Ohtsuka | G01N 21/648 250/459.1 |
| 2010/0133528 A1* | 6/2010 | Moon | G01N 27/227 257/43 |
| 2010/0140600 A1* | 6/2010 | Clough | B82Y 10/00 257/40 |
| 2010/0277740 A1 | 11/2010 | Hulteen | |
| 2010/0313752 A1* | 12/2010 | Powell et al. | 95/45 |
| 2011/0045601 A1 | 2/2011 | Gryska | |
| 2012/0071362 A1* | 3/2012 | Nhan | G01N 17/04 506/33 |
| 2013/0088244 A1 | 4/2013 | Gryska | |

FOREIGN PATENT DOCUMENTS

| | | |
|---|---|---|
| JP | 06-281610 | 10/1994 |
| JP | 2002-328110 | 11/2002 |
| JP | 2006-119153 | 5/2006 |
| JP | 2007-139447 | 6/2007 |
| WO | WO 2005/012397 | 2/2005 |
| WO | WO 2009/045733 | 4/2009 |
| WO | WO 2009/046011 | 4/2009 |
| WO | WO 2010/075333 | 7/2010 |
| WO | WO 2010/088088 | 8/2010 |
| WO | WO 2011/159480 | 12/2011 |
| WO | WO 2012/044419 | 4/2012 |
| WO | WO 2012/141925 | 10/2012 |

OTHER PUBLICATIONS

Budd, "Polymers of Intrinsic Microporosity (PIMs): robust, solution-processable, organic nanoporous Materials," Chem. Commun., 2004, pp. 230-231.

Budd, "Solution-Processed, Organophilic Membrane Derived from a Polymer of Intrinsic Microporosity", Advanced Materials, Mar. 2004, vol. 16, No. 5, pp. 456-459.

Budd, "Free volume and intrinsic microporosity in polymers", J of Materials Chemistry, 2005, vol. 15, pp. 1977-1986.

Kraus, "Plasmapolymerized silicon organic thin films from HMDSN for capacitive humidity sensors", Sensors and Actuators B, 2003, vol. 88, No. 3, pp. 300-311.

Matsuguchi, "Capacitive-Type Humidity Sensors Using Polymerized Vinyl Carboxylate", J. Electrochemical Soc, 1994, vol. 141, No. 3, pp. 614-618.

Matsuguchi, "Effect of the degree of cross-linking on the characteristics of a PVCA capacitive-type humidity sensor", Sensors and Actuators B, 1996, vol. 34, pp. 349-355.

McKeown, "Polymers of Intrinsic Microporosity (PIMs): Bridging the Void between Microporous and Polymeric Materials," Chem. Eur. J., 2005, vol. 11, No. 9, pp. 2610-2620.

Perez, "A poly(ethyleneterephthalate)-based humidity sensor", Sensors and Actuators B, Jul. 1997, vol. 42, No. 1, pp. 27-30.

International Search Report for International Application No. PCT/US11/50609 dated Jan. 24, 2012, 2 pages.

* cited by examiner

SENSOR ELEMENT, METHOD OF MAKING THE SAME, AND SENSOR DEVICE INCLUDING THE SAME

BACKGROUND

The ability to detect chemical vapors, especially volatile organic compounds (VOCs), is important in many applications including environmental monitoring and the like. Such detection and/or monitoring of organic vapors may find particular use in, for example, so called "end of service life indicators" which are desired for personal protective equipment such as respirators.

Many methods for the detection of chemical analytes have been developed including, for example, optical, gravimetric, and microelectromechanical (MEMS) methods. In particular, sensors that monitor electrical properties such as capacitance, impedance, resistance, etc., have been developed. Often, such sensors rely on the change that occurs in the electrical properties of a material upon adsorption of an analyte onto, or absorption of an analyte into, the material.

In one vapor sensor design, a layer of a polymer of intrinsic microporosity (PIM) is sandwiched between vapor impermeable electrodes held at a voltage bias, forming a capacitor. PIMs pack poorly at the molecular level, and hence are readily permeable by organic small molecules. As organic vapors accumulate (e.g., by absorption and/or adsorption) in the PIM layer they accumulate in the pores, and the dielectric constant of the material between the electrodes increases causing a change in capacitance that can be measured. However, if the electrodes are impermeable to organic vapors then there can be limited exposed surface of the PIM layer through which vapor absorption can occur.

To overcome this problem, discontinuous electrodes having openings therethrough and interdigitated electrode configurations have been used. However, it remains desirable to have sensor elements suitable for use in sensor devices for rapidly detecting organic vapors with good sensitivity.

SUMMARY

In one aspect the present disclosure, the present disclosure provides a sensor element comprising:
first conductive electrode having a first conductive member electrically coupled thereto;
an absorptive dielectric layer comprising a polymer of intrinsic microporosity; and
a second conductive electrode having a second conductive member electrically coupled thereto, wherein the second conductive electrode comprises at least one noble metal, wherein the second conductive electrode has a thickness of from 4 to 10 nanometers and is permeable to at least one organic vapor, and wherein the absorptive dielectric layer is at least partially disposed between the first conductive electrode and the second conductive electrode.

In another aspect, the present disclosure provides a method comprising steps of:
disposing an absorptive dielectric layer comprising a polymer of intrinsic microporosity on a first conductive electrode; and
disposing by thermal vapor deposition a second conductive electrode comprising at least one noble metal onto the absorptive dielectric layer, wherein the second conductive electrode has a thickness of from 4 to 10 nanometers after the thermal vapor deposition is complete, wherein the second conductive electrode is permeable to at least one organic vapor, and wherein the absorptive dielectric layer is at least partially disposed between the first conductive electrode and the second conductive electrode.

The method may further comprise: disposing a first conductive member on the first conductive electrode; and disposing a second conductive member on the second conductive electrode.

Advantageously, sensor elements according to the present disclosure include a porous electrode that allows organic vapors to diffuse through it, thereby increasing sensitivity of the sensor as compared to impermeable electrodes. The preparation of semi-permeable electrodes is achieved by using the thermal vapor deposition process according to the present disclosure, a process that uses no solvents.

Sensor elements according to the present disclosure are useful; for example, for making sensor devices.

Accordingly, in yet another aspect, the present disclosure provides a sensor device comprising:
a sensor chamber having an inlet opening,
a sensor element having a capacitance, disposed within the sensor chamber, and in fluid communication with the inlet opening, wherein the sensor element comprises:
first conductive electrode having a first conductive member electrically coupled thereto;
an absorptive dielectric layer comprising a polymer of intrinsic microporosity; and
a second conductive electrode having a second conductive member electrically coupled thereto, wherein the second conductive electrode comprises at least one noble metal, wherein the second conductive electrode has a thickness of from 4 to 10 nanometers and is permeable to at least one organic vapor, and wherein the absorptive dielectric layer is at least partially disposed between the first conductive electrode and the second conductive electrode;
an operating circuit in electrical communication with the sensor element,
whereby if the sensor element is connected to a source of electrical power, the operating circuit measures the capacitance of the sensor element.

As used herein,
the term "noble metal" refers to a metal selected from the group consisting of ruthenium, rhodium, palladium, osmium, iridium, platinum, and gold, in metallic form, unless otherwise specified;
the term "organic compound" refers to a compound that comprises carbon and hydrogen atoms; and
the term "permeable" in reference to a layer of a material means that in areas wherein the layer is present, the layer is sufficiently porous to be non-reactively permeable through its thickness (e.g., at 25° C.) to at least one organic compound.

The foregoing aspects and embodiments may be implemented in any combination thereof, unless such combination is clearly erroneous in view of the teachings of the present disclosure. The features and advantages of the present disclosure will be further understood upon consideration of the detailed description as well as the appended claims.

DETAILED DESCRIPTION

Figure 1:
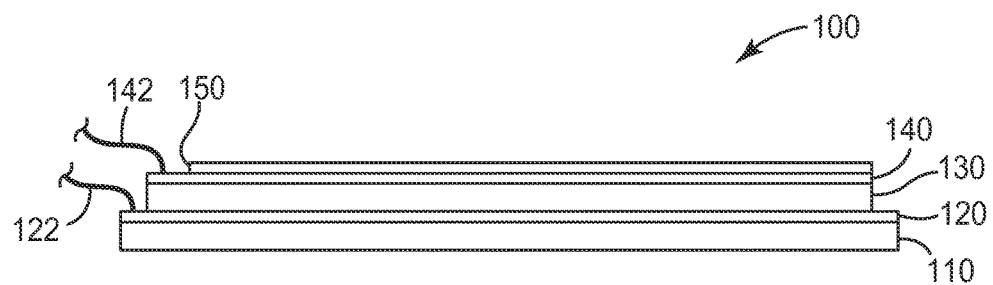
FIG. 1 is a schematic side view of an exemplary sensor element 100 according to the present disclosure.

Referring now to FIG. 1, sensor element 100 comprises dielectric 110 substrate supporting first conductive electrode 120 having a first conductive member 122 electrically coupled thereto. Absorptive dielectric layer 130 comprises a polymer of intrinsic microporosity, and is disposed between first conductive electrode 120 and second conductive electrode 140. Second conductive electrode 140 has a thickness of from 4 to 10 nanometers, comprises at least one noble metal (that is, one or more noble metals), and is permeable to at least one organic vapor. Second conductive member 142 is electrically coupled to second conductive electrode 140. Optional cover layer 150 is disposed on second conductive electrode 140. In the embodiment shown in FIG. 1, the first and second electrodes are generally planar, parallel, and disposed on opposite sides of the absorptive dielectric layer, although it will be recognized that other configurations are possible.

The sensor element is configured such that the absorptive dielectric layer is in sufficiently close proximity to the first conductive electrode and the second conductive electrode that the absorptive dielectric material contained in the layer will be capable of interacting with an electric field that is established by the electrodes. In operation of the sensor element, the absorptive dielectric layer exhibits a change in an electrical property upon absorption of one or more analytes (e.g., one or more organic vapors). In one embodiment, the electrical property is capacitance or a capacitance-related property as described below. Such a change in a capacitance-related property can be measured by imparting a charge differential between the first conductive electrode and the second conductive electrode (e.g., by imparting a voltage differential to the electrodes) and monitoring the property of the sensor element in response to the presence of the analyte. Such monitoring can be done by the use of an operating circuit, as described later herein.

The terms "capacitance" and "capacitance-related property" encompass any electrical property and the measurement thereof that is in general associated with the imparting of an electrical charge (whether static or time variant) and the monitoring of an electrical property during and/or after the imparting of the charge. Such properties include, for example, not only capacitance, but also impedance, inductance, admittance, current, resistance, conductance, etc., and may be measured according to various methods known in the art.

The absorptive dielectric layer (the term "layer" being used generically and encompassing any physical configuration) comprises at least in part an absorptive dielectric material. In this context, the term "absorptive dielectric material" means a material that is capable of absorbing an organic chemical analyte, and that can exhibit a measurable change in some electrical property of the material upon absorbing the organic analyte into the material.

While FIG. 1 depicts a parallel plate type of configuration, other configurations are also possible. For example, a configuration wherein the first and second electrodes are interdigitated is also possible and within the scope of the present disclosure.

In one embodiment, the absorptive dielectric material is chosen from the family of materials comprising so-called "polymers of intrinsic microporosity" (hereafter called PIMs). Such polymers include, but are not limited to, those disclosed in "Polymers of Intrinsic Microporosity (PIMs): Robust, Solution-Processable, Organic Microporous Materials," Budd et al., *Chem. Commun.,* 2004, pp. 230-231; in "Polymers of Intrinsic Microporosity (PIMs)," McKeown et al., *Chem. Eur. J.,* 2005, vol. 11, No. 9, 2610-2620; in US Patent Application Publication 2006/0246273 to McKeown et al.; and in Published PCT application No. WO 2005/012397A2 to McKeown et al.

PIMs can be formulated via the use of any combination of monomers that form a very rigid polymer within which there are sufficient structural features to induce a contorted structure. In various embodiments, PIMs can comprise organic macromolecules comprised of generally planar species connected by rigid linkers, said rigid linkers having a point of contortion such that two adjacent planar species connected by the rigid linkers are held in non-coplanar orientation. In further embodiments, such materials can comprise organic macromolecules comprised of first generally planar species connected by rigid linkers predominantly to a maximum of two other said first species, said rigid linkers having a point of contortion such that two adjacent first planar species connected by the rigid linkers are held in non-coplanar orientation. In various embodiments, such a point of contortion may comprise a spiro group, a bridged ring moiety or a sterically congested single covalent bond around which there is restricted rotation.

In a polymer with such a rigid and contorted structure, the polymer chains are unable to pack together efficiently, thus the polymer possesses intrinsic microporosity. Thus, PIMs have the advantage of possessing microporosity that is not significantly dependent on the thermal history of the material. PIMs thus may offer advantages in terms of being reproducibly manufacturable in large quantities, and in terms of not exhibiting properties that change upon aging, shelf life, etc.

In this context, the terms "microporous" and "microporosity" mean that the material has a significant amount of internal, interconnected pore volume, with the mean pore size (as characterized, for example, by sorption isotherm procedures) being less than about 100 nanometers (nm), typically less than about 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed. Without wishing to be limited by theory or mechanism, applicants consider that the disclosed sensor element, relying on a microporous dielectric material, may have advantageous properties with regard to the sensor of an organic analyte, in that a measurable change in an electrical property of the dielectric material may be caused by the presence of the analyte molecules in the pores. Thus, it may be possible to detect the analyte without the analyte molecules being required to be solubilized in the polymeric material itself to a sufficient extent to cause a change in a property of the polymeric material such as swelling and/or expansion (although such a phenomenon may also occur and may also contribute to a measurable electrical response). Such a microporous nature of the absorptive dielectric material may contribute to increased sensitivity of the dielectric material to small amounts of organic analyte.

In various embodiments, the PIM comprises a porosity of at least about 10 percent, at least about 20 percent, or at least about 30 percent (as characterized, for example, by sorption isotherm techniques, such as those using instruments available under the trade designation AUTOSORB from Quantachrome Instruments of Boynton Beach, Fla.). Such porosity can provide good response to low levels of organic chemical analytes. However, the material should not have such a high pore volume that it is difficult to avoid electrical shorting or arcing between the first conductive electrode and the second conductive electrode. Thus, in various embodiments, the material comprises a porosity of at most about 90 percent, at most about 60 percent or at most about 40 percent.

Again without being limited by theory or mechanism, the size and distribution of the internal pores may be such that at least some of the organic analyte molecules in at least some of the pores may form a more highly condensed state (e.g., a quasi-liquid state) than they would otherwise be in (e.g., than they would be in the environment in which the analyte is monitored). This may result in analyte molecules collecting in the internal pores in larger numbers and/or at a higher concentration than they are present in the environment being monitored; in addition, or instead, the analyte molecules in this state may exhibit a higher dielectric constant (relative permittivity) than in an uncondensed vaporous or gaseous state. Thus, a sensor element based on a microporous absorptive dielectric material with appropriately chosen size and distribution of pores may exhibit superior sensitivity to small quantities of organic analyte. In various embodiments, the PIM comprises an average pore size of less about 50 nm, less than about 20 nm, or less than about 10 nm. In various embodiments, the PIM comprises an average pore size of greater than about 0.3 nm, greater than about 0.5 nm, or greater than about 1.0 nm.

In one embodiment, the PIM is a hydrophobic material (e.g., a hydrophobic organic polymeric material), that will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

In one embodiment, the PIM comprises a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network as defined by applicant. However, if such a latex, sol-gel, etc., layer can be consolidated such that individual particles are no longer discernible, nor is it possible to discern areas of the assembly that were obtained from different particles, such a layer may then meet applicant's definition of a continuous matrix.

In certain embodiments, PIMs are soluble in common organic solvents and thus are amenable to conventional deposition processes such as coating.

In certain embodiments, after a PIM material is deposited (e.g., coated) or otherwise formed so as to comprise an absorptive dielectric layer, the material may be crosslinked using a suitable crosslinking agent, for example bis(benzonitrile)palladium(II) dichloride. This process may render the absorptive dielectric layer insoluble in organic solvents, and/or may enhance certain physical properties such as durability, abrasion resistance, etc., which may be desirable in certain applications.

In certain embodiments, the PIMs may be blended with other materials. For example, the PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-crosslinked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

The absorptive dielectric material may have any thickness, but typically is in a range of from about 100 to 3000 nanometers (nm). More typically, the absorptive dielectric material forms a layer having a thickness in a range of from 300 nm to 1000 nm, or even from 400 to 800 nm.

The absorptive layer may contain additives such as fillers, antioxidants, light stabilizers in addition to the PIM material, but since they may tend to interfere with proper operation of the sensor element such additives are typically minimized or not present. Combinations of PIM materials may be used.

In various embodiments, an additional layer or layers of material that is not an absorptive dielectric material may be provided in proximity to the absorptive dielectric layer. Such a layer or layers may be provided for any of a variety of reasons; for example, as a protective layer or as a tie layer to improve adhesion.

In various embodiments, multiple individual layers of absorptive dielectric material can be used. For example, multiple layers of PIM materials can be used. Alternatively, one or more layers of some other absorptive dielectric material can be used in addition to a layer of PIM material. The various layers of absorptive dielectric material can be in direct contact with each other; or, they can be separated by a layer or layers present for some other purpose (e.g., passivation layers, tie layers, as described herein).

The first conductive electrode can comprise any suitable conductive material. Combinations of different materials (conductive and/or nonconductive) can be used, as different layers or as a mixture, as long as sufficient overall conductivity is provided, Typically, the first conductive electrode has a sheet resistance of less than about $10^7$ ohms/square. Examples of materials that can be used to make the first conductive electrode and/or second conductive electrode include, but are not limited to, organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable conductive materials include for example aluminum, nickel, titanium, tin, indium-tin oxide, gold, silver, platinum, palladium, copper, chromium and combinations thereof.

The first conductive electrode can be of any thickness as long as it is conductive; for example, in a thickness in a range of from at least 4 nm to 400 nm, or from 10 nm to 200 nm. If the first conductive electrode is thicker than about 1000 nm or greater, it can become difficult for the second conductive electrode to bridge the edge of the electrode to make a conductive path. If the first conductive electrode is too thick, then the edge of the first conductive electrode may be sloped so that the second conductive electrode can make a continuous conductive path.

The second conductive electrode comprises at least one noble metal. In some embodiments, the second conductive electrode may have a noble metal content of at least 50, 60, 70, 80, 90, 95, 99, or even at least 99.9 percent by weight. In some embodiments, the second conductive electrode consists of, or consists essentially of gold, palladium, platinum, or a combination thereof. The second layer may include additional components as long as it remains permeable to at least one organic analyte. Combinations of different materials (conductive and/or nonconductive) can be used, as different layers or as a mixture, as long as sufficient overall conductivity and permeability is provided. Typically, the second conductive electrode has a sheet resistance of less than about $10^7$ ohms/square.

The second conductive electrode has a thickness in a range of from 4 to 10 nm. In some embodiments, the second conductive electrode has a thickness in a range of from 5, 6, or 7 nm up to 7, 8, 9, or 10 nm. For example, the second conductive electrode may have a thickness in a range of from or from 5 to 8 nm, or from 6 to 7 nm. Greater thicknesses generally have undesirably low levels of permeability, while lesser thicknesses may become insufficiently conductive and/or difficult to electrically connect to the second conductive member. Since the second conductive electrode is permeable, the first electrode typically comprises a continuous, uninterrupted layer, but it may contain openings or other interruptions if desired.

The second conductive electrode can be prepared by a thermal vapor deposition process. In thermal vapor deposition, the material used to make the second electrode is heated under vacuum until it vaporizes and deposits on an appropriate component of the sensing element (e.g., the absorptive dielectric layer or the optional cover layer). Any suitable source of heating may be used; examples include resistive heating, laser heating, and e-beam heating (also termed e-beam evaporation). Thermal vapor deposition is generally carried out at pressures of about $10^{-5}$ or $10^{-6}$ torr (1 mPa-0.1 mPa), or lower.

Thermal vapor deposition differs from sputter deposition. In sputter deposition, high energy atoms are bombarded into a target or source which then ejects material that deposits on a substrate. Typical pressures involved in sputter deposition are in the range of $10^{-2}$-$10^{-4}$ torr (1 Pa-0.1 Pa) or higher.

In an exemplary process for making such a sensor element, a dielectric substrate is provided (which may be a continuous slab, layer or film of material) that is in proximity to the first electrode and that may serve to provide physical strength and integrity to the finished sensor element. Any suitable material may be used, including glass, ceramic, plastic, etc. In large scale production, a polymeric film (such as polyester) may be used. In some embodiments, the dielectric substrate is an analyte-permeable material (e.g., silicone rubber or a microporous membrane).

Improvement in performance of sensor elements according to the present disclosure can generally be achieved by heating the second electrode, typically in combination with other components of the sensor element at a temperature of from 100° C. to 250° C. after deposition of the second electrode. Soak times at these temperatures can have any duration, but typically fall in a range of from minutes to several hours.

In one embodiment, the first conductive electrode is provided on the dielectric substrate. The conductive layer may comprise any of the materials mentioned above, including blends or mixtures of conductive and nonconductive materials, and may be deposited by any suitable method, including but not limited to spin coating, dip coating, screen printing, transfer coating, sputter-coating, physical vapor deposition, chemical vapor deposition, or a combination of two or more of such methods. In an alternate embodiment, the conductive layer may be provided by placing a premade film (e.g. a metal foil, conductive tape, etc.) atop the dielectric substrate. This first conductive electrode may be provided as a continuous layer or as a discontinuous layer, as previously described.

In one embodiment, the first conductive electrode is provided such that the first conductive electrode is in proximity to, and/or in contact with, at least a portion of the dielectric substrate. In an alternative embodiment, an optional layer is present between at least a portion of the first conductive electrode, and the dielectric substrate. Such an optional layer may be used for any purpose (e.g., such as improving the bond between first conductive electrode and the dielectric substrate), as long as the layer does not interfere with the functioning of the sensor element.

The first and second conductive members may be electrically coupled to the first and second conductive electrodes at any appropriate point during assembly of the sensor element. For example, the first conductive member may be attached to the first conductive electrode immediately after deposition of the first conductive electrode and before deposition of the absorptive dielectric layer. In alternative embodiment, the absorptive dielectric layer may be deposited on the first conductive electrode such that an area of the first conductive electrode is left exposed for attachment to the first conductive member. Similarly, the second conductive member may be attached to the second conductive electrode immediately after deposition of the second conductive electrode and before deposition of the optional cover layer, or the optional cover layer may be deposited on the second conductive electrode such that an area of the second conductive electrode is left exposed for attachment to the second conductive member.

In one embodiment, the absorptive dielectric material is placed in proximity to the first conductive electrode by a coating process; for example, including but not limited to solvent coating, spin coating, dip coating, transfer coating, screen printing, and the like. In certain embodiments, the dielectric material is deposited in such a manner as to minimize the presence of defects, pinholes, etc., that might serve to compromise the performance of the sensor element. In a particular embodiment, the absorptive dielectric layer comprises a polymer of intrinsic microporosity that is deposited by coating a solution of PIM material upon a suitable dielectric substrate and allowing the solution to dry so as to form a solid layer comprising the PIM material. Optionally, the construction may be heated to a temperature in a range of from 100° C. to 200° C. to further dry the coated PIM material.

An absorptive dielectric layer can also be provided by other methods. For example, a preformed film of absorptive dielectric material can be placed upon the second surface of the first conductive electrode. In an alternative embodiment, the absorptive dielectric material can be provided in particulate form (e.g. as a powder, as a suspension, or as a sol) and deposited in such a form onto a first conductive electrode so as to form a particulate coating. If desired, such a material can be consolidated so as to form a continuous matrix of absorptive dielectric material.

An optional protective cover or barrier layer can be provided in proximity to at least one of the first or second conductive electrodes. For example, in one embodiment, a cover layer can be placed atop the second conductive electrode, leaving an area of second conductive electrode accessible for electrical contact with the second conductive member electrical contact. Any such cover layer should not significantly interfere with the functioning of the sensor element. For example, if the sensor element is configured such that an analyte of interest must pass through cover layer in order to reach the absorptive dielectric layer, the cover layer should be sufficiently permeable to the analyte.

The optional cover layer may be deposited by any method known in the art, including coating (e.g. spin coating, dip coating, solvent coating, vapor coating, transfer coating, screen printing, flexographic printing, and the like). In an alternate embodiment, the cover layer can comprise a pre-made layer (e.g. a film or tape) that is placed upon the second conductive electrode. In one embodiment, the cover layer is provided such that the cover layer is in direct contact with at least a portion of a major surface of the second conductive electrode. The cover layer may be the outermost layer of the sensor element, or may itself receive additional coatings or layers if desired.

In one embodiment, the first conductive electrode and the absorptive dielectric layer are in direct contact, with no interposing layer(s) therebetween. Likewise, in one embodiment, the second conductive electrode and the absorptive dielectric layer are in direct contact, with no interposing layer(s) therebetween. Such embodiments are pictured in FIG. 1. However, it is also contemplated that other, optional layers may be present between the first conductive electrode and the absorptive dielectric layer, and/or between the second conductive electrode and the absorptive dielectric layer. In such a case, either or both of the electrodes may not be in direct contact with some or all of a surface of the absorptive dielectric material. For example, a tie layer or layers may be used to improve the bonding between an electrode and the absorptive dielectric layer. Or, a passivation layer or layers (for example, a layer of silicon dioxide) may be placed in between a surface of the absorptive dielectric layer and an electrode surface, in order to minimize the possibility of arcing between the electrodes. In some embodiments, multiple such optional layers may be used; alternatively a single layer may serve multiple functions. Any such optional layer or layers such as the aforementioned tie layers, passivation layers, protective layers, cover layers, etc., may be used, for whatever purpose, as long as they do not significantly interfere with the desired functioning of the sensor element. For example, an optional layer should be sufficiently permeable to an analyte of interest if the sensor element is configured such that the analyte must pass through the optional layer in order to reach the absorptive dielectric layer.

In general, the edges of the first and/or second electrodes and/or absorptive dielectric layer can be aligned flush with each other, or, they may be recessed and/or extended relative to each other or any other layers that may be present.

In the deposition of the absorptive dielectric material onto the first conductive electrode, an electrically accessible area may be provided on the first conductive electrode to enable electrical contact between the electrode and an operating circuit. Similarly, if a cover layer is placed atop second conductive electrode, an electrically accessible area may be similarly provided. Such electrically accessible areas can be provided in any convenient location. In one embodiment, a connecting device (e.g. a contact pad, tab, or the like) may be placed in electrical contact with accessible area of first conductive electrode. Similarly, a connecting device may be placed likewise in contact with an accessible area of the second conductive electrode.

Upon absorption of sufficient analyte by the absorptive dielectric layer, a detectable change in an electrical property associated with the sensor element (including but not limited to, capacitance, impedance, inductance, admittance, current, or resistance) may occur. Such a detectable change may be detected by an operating circuit that is in electrical communication with the first and second conductive electrodes. In this context, "operating circuit" refers generally to an electrical apparatus that can be used to apply a voltage to the first conductive electrode and the second conductive electrode (thus imparting a charge differential to the electrodes), and/or to monitor an electrical property of the sensor element, wherein the electrical property may change in response to the presence of an organic analyte. In various embodiments, the operating circuit may monitor any or a combination of inductance, capacitance, voltage, resistance, conductance, current, impedance, phase angle, loss factor, or dissipation.

Such an operating circuit may comprise a single apparatus which both applies voltage to the electrodes, and monitors an electrical property. In an alternative embodiment, such an operating circuit may comprise two separate apparatuses, one to provide voltage, and one to monitor the signal. The operating circuit is typically electrically coupled to first conductive electrode and to second conductive electrode by conductive members.

Figure 2:
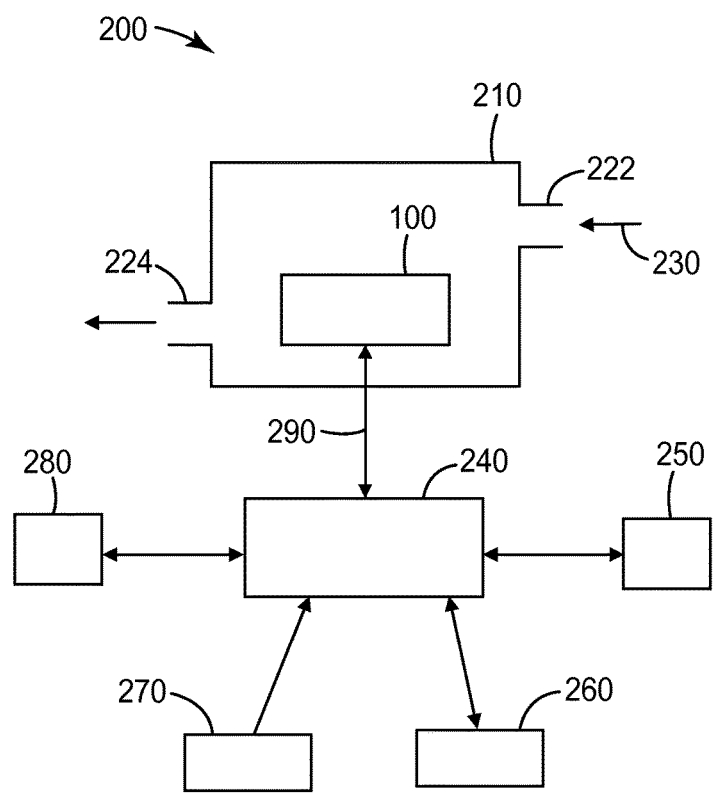
FIG. 2 is a schematic view of an exemplary sensor device 200 according to the present disclosure.

Referring now to FIG. 2, exemplary sensor device 200 includes a sensor chamber 210 having an inlet opening 222 and optional outlet opening 224. Sensor element 100 (as described hereinabove) is disposed within the sensor chamber 210, and is in fluid communication with the inlet opening 222 and optional outlet opening 224, if present. In typical operation, a sample containing analyte 230 enters sensing chamber 210, where it contacts sensor element 100. An operating circuit 240 is in electrical communication via conductive pathways 290 with sensor element 100. When connected to a source of electrical power 270, operating circuit 240 measures the capacitance of sensor element 100. In some embodiments, operating circuit 240 is communicatively coupled to data storage device 250, controller device 280, and/or display device 260.

In operation, the operating circuit 240 is in electrical communication with a source of electrical power 270.

Exemplary sources of electrical power include batteries, plug in power supplies, generators, hardwired power supplies, and RF generators (if the operating circuit includes an RF receiver).

The sensor chamber can be constructed of any solid material that is impermeable to the analyte. Examples include metal and/or plastic. Exemplary display devices 260 include LED displays, LCD displays, CRT displays, galvanic meters, and printers. Controller device 280, if present, includes hardware and/or software that directs operation of the operating circuit. Exemplary data storage devices 250 include flash memory cards, hard disks, digital tape, and CD R media.

In an alternative embodiment, the operating circuit may be provided in direct contact with the first and/or the second conductive electrode, either via connecting members, or by contacting some portion of the operating circuit directly to an electrically accessible area of each electrode. For example, an operating circuit can be provided that resides on a circuit board or a flexible circuit (either of which can also serve as the dielectric substrate). The first conductive electrode can then be deposited directly onto the dielectric substrate such that it is in direct contact with a portion of the operating circuit.

Sensor elements and sensor devices according to the present disclosure can be used to detect and/or monitor (whether qualitatively or quantitatively) the presence of an organic analyte or analytes. Such analytes can include, but are not limited to, hydrocarbons, fluorocarbons, alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile and the like. Organic analytes can be relatively nonpolar organic molecules or relatively polar organic molecules. Analytes are typically vapors; that is, molecules that are capable of condensing to form a solid or liquid under the ambient conditions of temperature and pressure that the analyte is experiencing (e.g., toluene, acetone, or heptane).

Select Embodiments of the Disclosure

In a first embodiment, the present disclosure provides a sensor element comprising:
first conductive electrode having a first conductive member electrically coupled thereto;
an absorptive dielectric layer comprising a polymer of intrinsic microporosity; and
a second conductive electrode having a second conductive member electrically coupled thereto, wherein the second conductive electrode comprises at least one noble metal, wherein the second conductive electrode has a thickness of from 4 to 10 nanometers and is permeable to at least one organic vapor, and wherein the absorptive dielectric layer is at least partially disposed between the first conductive electrode and the second conductive electrode.

In a second embodiment, the present disclosure provides a sensor element according to the first embodiment, further comprising a dielectric substrate supporting the first conductive electrode.

In a third embodiment, the present disclosure provides a sensor element according to the second embodiment, wherein the dielectric substrate comprises a polymeric film.

In a fourth embodiment, the present disclosure provides a sensor element according to any one of the first to third embodiments, wherein the at least one noble metal comprises at least 99 percent by weight of the second conductive electrode.

In a fifth embodiment, the present disclosure provides a sensor element according to any one of the first to fourth embodiments, wherein the second conductive electrode comprises gold, palladium, platinum, or a combination thereof.

In a sixth embodiment, the present disclosure provides a sensor element according to any one of the first to fifth embodiments, wherein the polymer of intrinsic microporosity comprises organic macromolecules comprised of generally planar species connected by rigid linkers, said rigid linkers having a point of contortion such that two adjacent planar species connected by one of the rigid linkers are held in non-coplanar orientation.

In a seventh embodiment, the present disclosure provides a sensor element according to any one of the first to sixth embodiments, wherein the first conductive electrode comprises at least one noble metal, and wherein the first conductive electrode has a thickness of from 4 to 10 nanometers, or from 5 to 8 nanometers, or from 6 to 7 nanometers, and is permeable to at least one organic vapor.

In a eighth embodiment, the present disclosure provides a sensor element according to any one of the first to seventh embodiments, wherein the second conductive electrode is coextensive with a major surface of the absorptive dielectric layer.

In a ninth embodiment, the present disclosure provides a method comprising steps of:
disposing an absorptive dielectric layer comprising a polymer of intrinsic microporosity on a first conductive electrode; and
disposing by thermal vapor deposition a second conductive electrode comprising at least one noble metal onto the absorptive dielectric layer, wherein the second conductive electrode has a thickness of from 4 to 10 nanometers after the thermal vapor deposition is complete, wherein the second conductive electrode is permeable to at least one organic vapor, and wherein the absorptive dielectric layer is at least partially disposed between the first conductive electrode and the second conductive electrode.

In a tenth embodiment, the present disclosure provides a method according to the ninth embodiment, wherein the first conductive electrode is supported on a dielectric substrate.

In an eleventh embodiment, the present disclosure provides a method according to the tenth embodiment, wherein the dielectric substrate comprises a polymeric film.

In a twelfth embodiment, the present disclosure provides a method according to any one of the ninth to eleventh embodiments, wherein the steps are sequential.

In a thirteenth embodiment, the present disclosure provides a method according to any one of the ninth to twelfth embodiments, wherein the at least one noble metal comprises at least 99 percent by weight of the second conductive electrode.

In a fourteenth embodiment, the present disclosure provides a method according to any one of the ninth to thirteenth embodiments, wherein the second conductive electrode comprises gold, palladium, platinum, or a combination thereof.

In a fifteenth embodiment, the present disclosure provides a method according to any one of the ninth to fourteenth embodiments, wherein the polymer of intrinsic microporosity comprises organic macromolecules comprised of generally planar species connected by rigid linkers, said rigid linkers having a point of contortion such that two adjacent planar species connected by the rigid linkers are held in non-coplanar orientation.

In a sixteenth embodiment, the present disclosure provides a method according to any one of the ninth to fifteenth embodiments, wherein the first conductive electrode comprises at least one noble metal, and wherein the first conductive electrode has a thickness of from 4 to 10 nanometers and is permeable to at least one organic vapor.

In a seventeenth embodiment, the present disclosure provides a method according to any one of the ninth to sixteenth embodiments, wherein the second conductive electrode is coextensive with a major surface of the absorptive dielectric layer.

In an eighteenth embodiment, the present disclosure provides a method according to any one of the ninth to seventeenth embodiments, further comprising heating at least the second electrode at a temperature in a range of from 100 to 250 degrees Celsius.

In an nineteenth embodiment, the present disclosure provides a sensor device comprising:
 a sensor chamber having an inlet opening,
 a sensor element having a capacitance, disposed within the sensor chamber, and in fluid communication with the inlet opening, wherein the sensor element comprises:
  first conductive electrode having a first conductive member electrically coupled thereto;
  an absorptive dielectric layer comprising a polymer of intrinsic microporosity; and
  a second conductive electrode having a second conductive member electrically coupled thereto, wherein the second conductive electrode comprises at least one noble metal, wherein the second conductive electrode has a thickness of from 4 to 10 nanometers and is permeable to at least one organic vapor, and wherein the absorptive dielectric layer is at least partially disposed between the first conductive electrode and the second conductive electrode;
 an operating circuit in electrical communication with the sensor element,
 whereby if the sensor element is connected to a source of electrical power, the operating circuit measures the capacitance of the sensor element.

In a twentieth embodiment, the present disclosure provides a sensor device according to the nineteenth embodiment, wherein the sensor chamber further comprises an outlet opening in fluid communication with the inlet opening.

In a twenty-first embodiment, the present disclosure provides a sensor device according to the nineteenth or twentieth embodiment, further comprising a display device in communicatively coupled with the operating circuit.

In a twenty-second embodiment, the present disclosure provides a sensor device according to any one of the nineteenth to twenty-first embodiments, wherein the second conductive electrode comprises gold, palladium, platinum, or a combination thereof.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight. Solvents and other reagents used were obtained from Sigma-Aldrich Chemical Company of Milwaukee, Wis., unless specified differently.

As used hereinbelow, the Small Area Bottom Electrode is equivalent to a first conductive electrode, the Small Area Top Electrode is equivalent to a second conductive electrode; the Small Area Top Connecting Electrode is equivalent to the second conductive member; and the first conductive member is equivalent to a spring-loaded contact pin used to couple the sensor electrically to the operating circuit.

Materials

ACRODISC filter: ACRODISC 25 MM SYRINGE FILTER WITH 1 MICRON GLASS FIBER MEMBRANE from PALL Life Sciences of Ann Arbor, Mich.
Activated Carbon/Silica Gel: activated carbon/silica gel obtained as AGM P/N 4095, 0.5 g packets from AGM Container Controls, Inc. of Tucson, Ariz.
AGILENT LCR meter: model E4980A Precision LCR Meter from Agilent Technologies, Inc., Santa Clara, Calif.
Aluminum: obtained as shot, 4-8 mm, Puratronic grade 99.999 percent from Alfa Aesar of Ward Hill, Mass.
ALCONOX LIQUI-NOX: detergent obtained from Alconox, Inc. of White Plains, N.Y.
DRIERITE: desiccant obtained from W.A. Hammond Drierite Co. Ltd. of Xenia, Ohio.
Gold: obtained as metal spatters, 99.999 percent typical purity from Cerac Inc. of Milwaukee, Wis.
Nickel: obtained as 3.175 mm×3.175 mm slug, 99.995 percent pure from Alfa Aesar.
Palladium: obtained as 99.99% typical purity, 3-6 mm pieces, from Cerac Specialty Inorganics of Milwaukee, Wis.
Platinum obtained as 0.125×0.125 mm pieces, 99.99% typical purity, from Williams Advanced Materials of Buffalo, N.Y.
PGO glass slides: glass number 0050-0050-0010-GF-CA, 50 mm×50 mm, 1.1 mm thick, material C-263, surface 80/50, obtained from Precision Glass & Optics of Santa Ana, Calif.
Protek multimeter: Model 6300 5 in 1, Digital Multimeter, obtained from Protek Test and Measurement of Englewood, N.J.
Titanium: obtained as titanium slug, 9.5 mm×9.5 mm, 99.9+ percent purity from Alfa Aesar.

Preparation of PIM

PIM material was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459.

5,5',6,6'-tetrahydroxy-3,3,3',3'-tetramethyl-1,1'-spirobisindane (40.000 g) was combined with 23.724 g of tetrafluoroterephthalonitrile, 97.373 g potassium carbonate, and 1016.8 g of N,N-dimethylformamide, and the mixture was reacted at 68° C. for 72 hours. The polymerization mixture was poured into water, and the precipitate was isolated by vacuum filtration. The resulting polymer was twice dissolved in tetrahydrofuran, precipitated from methanol, and air dried at room temperature. A yellow solid product was obtained having a number-average molecular weight of approximately 41,900 g/mole, as determined by gel permeation chromatography analysis using light scattering detection.

Comparative Examples A-C and Examples 1-2

Sensor elements were prepared on PGO glass slides which were cleaned by soaking them for 30 to 60 minutes in Alconox Liqui-Nox detergent solution, then scrubbing each side of the slides with a bristle brush, rinsing them under warm tap water followed by a final rinse with deionized water (DI water). The slides were allowed to air dry covered to prevent dust accumulation on the surface. The dry, clean slides were stored in 7.6 cm (3 inch) wafer carriers obtained from Entegris of Chaska, Minn.

Figure 3:
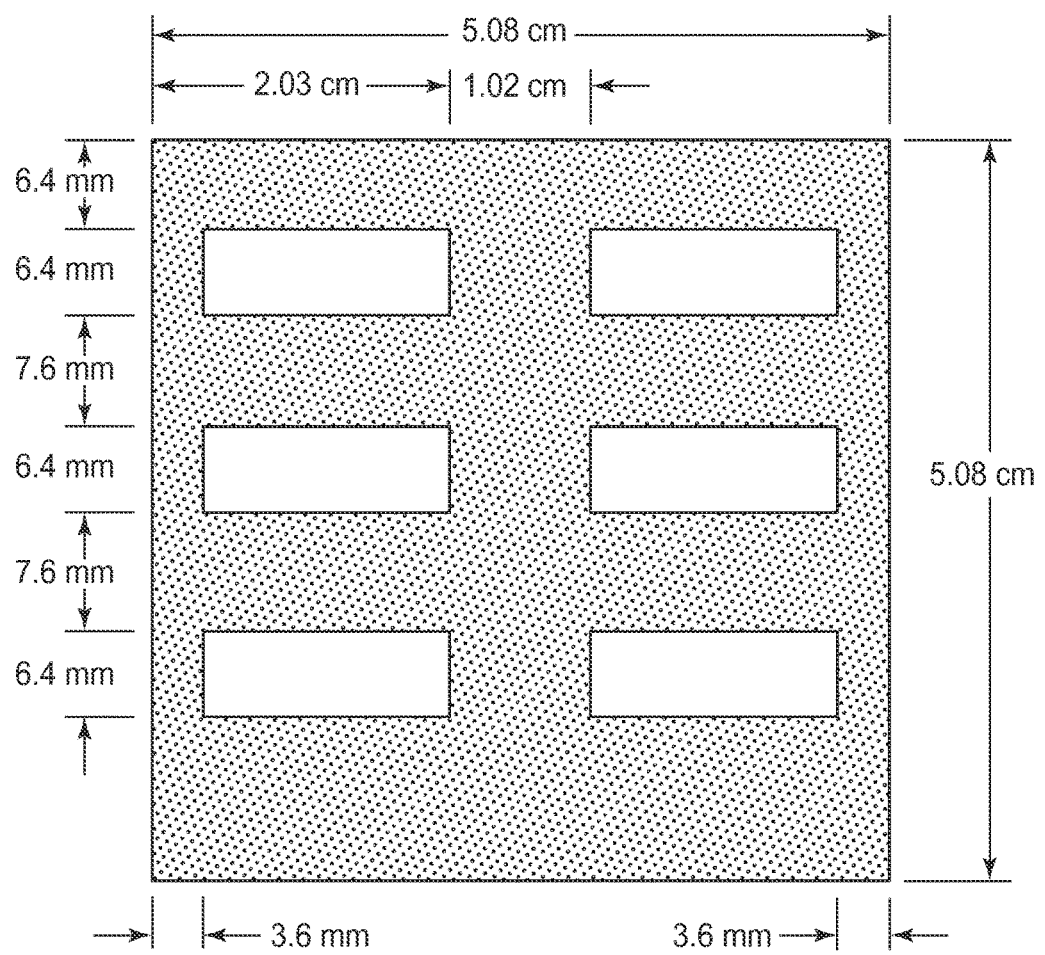
FIGS. 3-5 are plan views of metal aperture masks used in the examples.

A bottom electrode was deposited onto the PGO glass slide by e-beam evaporative coating 10.0 nanometers (nm) of titanium at a rate of 0.1 nanometers per second (nm/sec) followed by 150.0 nm of aluminum at 0.5 nm/sec using a Small Area Bottom Electrode (SABE) mask prepared from 50 gauge stainless steel laser cut in the dimensions of FIG. 3. All masks were deburred before using to minimize the possibility of shorts caused by sharp edges in the mask. The deposition process was controlled using an INFICON XTC/2 THIN FILM DEPOSITION CONTROLLER from INFICON of East Syracuse, N.Y.

A PIMS solution of 5.5 percent by weight in chlorobenzene was prepared by mixing the components in a small jar and placing it on a roller mill (Mini Bottle Roller number 348920 from Wheaton Science Products, Millville, N.J.) for about 3 hours then filtering through a one-micron Acrodisc filter. The solution was allowed to sit over night so that any bubbles that formed could escape.

Samples were spin-coated with PIMS using a Model WS 400B-8NPP/LITE spin coater from Laurell Technologies Corporation of North Wales, Pa. To coat a sample, it was placed in the spin coater and about 0.5 ml of chlorobenzene was placed on the sample. Each sample was spun for 15 seconds at 300 rpm, then 45 seconds at 2000 rpm. The solvent was dispensed during the first 15 seconds of the spin coating profile. Then, for all samples, the PIMS solution was dispensed during the first 15 seconds while the sample was spinning A spin profile of 15 seconds at 300 rpm then 45 seconds at 2000 rpm was used for all samples. After spin coating, PIMS thickness measurements were made using a Model XP-1 Profilometer from AMBiOS Technology of Santa Cruz, Calif. by removing a small section of the coating with an acetone soaked cotton swab. The parameters used in the thickness measurement were a scan speed of 0.1 mm/sec, a scan length of 5 mm, a range of 10 micrometers, a stylus force of 0.20 mg and a filter level of 4. All samples were baked for 1 hour at 100° C. after coating.

Figure 4:
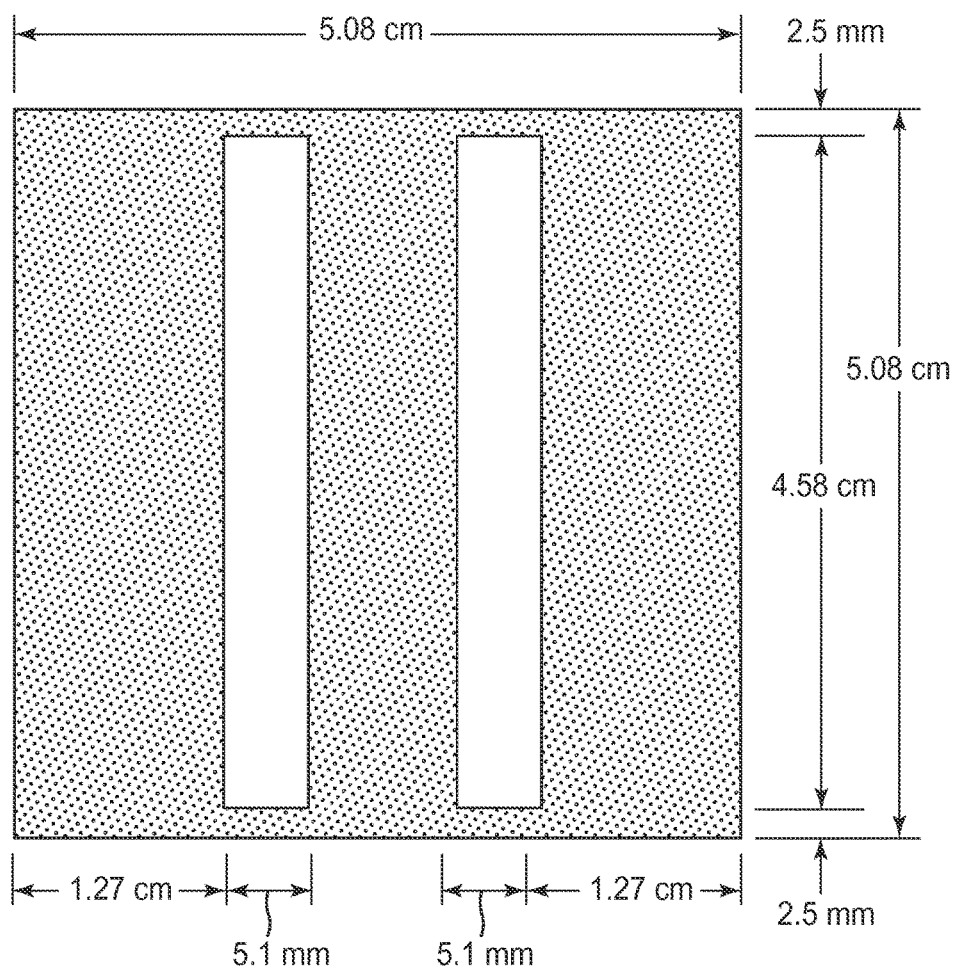

To prepare the top electrode, a Small Area Top Electrode (SATE) mask was made from 24 gauge stainless steel by laser milling the pattern shown in FIG. 4. The top electrode was vapor deposited through the SATE mask using thermal deposition of gold at various thicknesses. A deposition rate of 0.1 nm/sec was used for all thicknesses. After depositing the active electrode, a connecting electrode was deposited by thermal vapor coating 10.0 nm of titanium at a rate of 0.1 nm/sec followed by 150.0 nm of aluminum at 0.5 nm/sec through a Small Area Top Connecting Electrode (SATCE) mask prepared by laser milling from 50 gauge stainless steel using the pattern in FIG. 5. Both deposition processes were controlled using an INFICON XTC/2 THIN FILM DEPOSITION CONTROLLER.

This sensor production process produced a set of six sensor elements of approximately 4.5 mm×6 mm active area (area under the overlapping top and bottom electrodes that was not covered by the connecting electrode) on an approximately 50 mm×50 mm glass substrate. Individual sensor elements were produced by dicing the sample using a standard glass scoring cutter on the back (inactive side) while supporting the sensor elements so that their front (active) surfaces would not be damaged.

Before dicing the samples into individual sensor elements, PIMS covering the bottom electrode contact area was removed with a cotton swab wet with acetone and a simple electrical test was made using a Protek multimeter. The resistance was measured between two adjacent sensor elements to determine the relative resistance of the very thin gold top electrode. The results of those measurements are shown in Table 1. After dicing, the individual sensor elements were tested using the same resistance meter. A capacitance reading could not be obtained for sensor elements of Comparative Examples A and B. Some specimens according to Comparative Example C and Example 2 shorted. Example 1 had a capacitance of about 1.6 nanofarads (nF). After dicing, the samples were stored in sealed glass jars in the dark with 20 packets of an Activated Carbon/Silica Gel to protect the sensor elements from unintended exposure to organic vapors or moisture. The samples were stored in this manner until testing for organic vapor response.

TABLE 1

| | PIMS LAYER THICKNESS, nm | GOLD ELECTRODE THICKNESS, nm | RESISTANCE BETWEEN ELECTRODES, ohms |
|---|---|---|---|
| COMPARATIVE EXAMPLE A | 589 | 1.0 | resistance reading could not be obtained |
| COMPARATIVE EXAMPLE B | 593 | 2.0 | resistance reading could not be obtained |
| COMPARATIVE EXAMPLE C | 585 | 3.0 | 400 |
| EXAMPLE 1 | 593 | 4.0 | 150 |
| EXAMPLE 2 | 617 | 5.0 | 70 |

All tests were performed in air that had been passed over Drierite to remove moisture, and passed over activated carbon to eliminate any organic contaminates. The testing chamber allowed the measurement of four sensor specimens at a time. Spring-loaded contact pins were used to couple the sensor electrically to the operating circuit. Vapor tests were conducted using a 10 L/minute dry air flow through the system. Various vapor levels were generated using a KD Scientific syringe pump (available from KD Scientific Inc. of Holliston, Mass.) fitted with a 500 microliter gas tight syringe (obtained from Hamilton Company of Reno, Nev.). The syringe pump delivered the organic liquid onto a piece of filter paper suspended in a 500 ml three-necked flask through a piece of Teflon tubing (supplied by Hamilton Company of Reno, Nev., part number KF28TF NDL) fitted with a Luer Lock to allow connection to the syringe. The flow of dry air past the paper vaporized the solvent. Delivering the solvent at different rates by controlling the syringe pump generated different concentrations of vapor. The syringe pump was controlled by a LABVIEW (software available from National Instruments of Austin, Tex.) program that allowed vapor profiles to be generated during a test run. A MIRAN IR analyzer (available from Thermo Fischer Scientific, Inc. of Waltham, Mass.) was used to verify the set concentrations. The capacitance and dissipation factors were measured with an Agilent LCR meter applying one volt at 1000 Hz across the top and bottom electrodes. This data was collected and stored using the same LABVIEW program that controlled the syringe pump.

The initial capacitance and dissipation factors for four replicate sensor elements of Example 1, 2, and 3 and Comparative Examples A, B, and C were recorded after they had been in the dry air of the testing chamber for about 5 to 10 minutes. These values are reported in Table 2 (below).

TABLE 2

| | REPLICATE | | | |
|---|---|---|---|---|
| | A | B | C | D |
| EXAMPLE 1 | | | | |
| Initial Capacitance, picofarads (pF) | 1206.5 | 1221.6 | 1208.3 | 1256.9 |
| Initial Dissipation Factor | 0.042 | 0.002 | 0.002 | 0.007 |
| EXAMPLE 2 | | | | |
| Initial Capacitance, pF | 1167.8 | 1195.5 | 1172.8 | 1190.0 |
| Initial Dissipation Factor | 0.001 | 0.002 | 0.001 | 0.001 |
| COMPARATIVE EXAMPLE A | | | | |
| Initial Capacitance, pF | 1.10 | 0.69 | 1.09 | 0.59 |
| Initial Dissipation Factor | 0.025 | 0.055 | 0.027 | 0.034 |
| COMPARATIVE EXAMPLE B | | | | |
| Initial Capacitance, pF | 1.21 | 0.93 | 1.28 | 0.86 |
| Initial Dissipation Factor | 0.130 | 0.225 | 0.140 | 0.244 |
| COMPARATIVE EXAMPLE C | | | | |
| Initial Capacitance, pF | 1260.0 | 1231.4 | 1249.8 | 1238.7 |
| Initial Dissipation Factor | 0.005 | 0.003 | 0.003 | 0.003 |

$\Delta C/C_O$, the change in capacitance from the initial value divided by the initial value, was determined from the raw capacitance data. Results using methyl ethyl ketone (MEK) are reported in Table 3 (below).

TABLE 3

| EXAMPLE | MEK CONCENTRATION, parts per million (ppm) | REPLICATE, $\Delta C/C_O$ | | | |
|---|---|---|---|---|---|
| | | A | B | C | D |
| 2 | 0 | 0 | 0 | 0 | 0 |
| 2 | 6 | 0.044 | 0.052 | 0.088 | 0.098 |
| 2 | 12 | 0.119 | 0.137 | 0.147 | 0.148 |
| 2 | 25 | 0.190 | 0.206 | 0.203 | 0.204 |
| 2 | 50 | 0.260 | 0.271 | 0.265 | 0.266 |
| 2 | 100 | 0.332 | 0.339 | 0.331 | 0.331 |
| 2 | 200 | 0.401 | 0.405 | 0.397 | 0.398 |
| 2 | 400 | 0.466 | 0.467 | 0.459 | 0.460 |
| 1 | 0 | 0 | 0 | 0 | 0 |
| 1 | 6 | 0.100 | 0.098 | 0.103 | 0.107 |
| 1 | 12 | 0.151 | 0.150 | 0.147 | 0.147 |
| 1 | 25 | 0.208 | 0.206 | 0.203 | 0.202 |
| 1 | 50 | 0.268 | 0.267 | 0.264 | 0.263 |
| 1 | 100 | 0.336 | 0.335 | 0.332 | 0.331 |
| 1 | 200 | 0.404 | 0.402 | 0.399 | 0.398 |
| 1 | 400 | 0.466 | 0.465 | 0.461 | 0.461 |
| Comp. Ex. C | 0 | 0 | 0 | 0 | 0 |
| Comp. Ex. C | 6 | 0.080 | 0.071 | 0.095 | 0.087 |
| Comp. Ex. C | 12 | 0.134 | 0.135 | 0.139 | 0.142 |
| Comp. Ex. C | 25 | 0.195 | 0.200 | 0.199 | 0.203 |
| Comp. Ex. C | 50 | 0.257 | 0.264 | 0.261 | 0.266 |
| Comp. Ex. C | 100 | 0.324 | 0.332 | 0.329 | 0.334 |
| Comp. Ex. C | 200 | 0.389 | 0.398 | 0.394 | 0.400 |
| Comp. Ex. C | 400 | 0.452 | 0.462 | 0.457 | 0.464 |
| Comp. Ex. B | 0 | 0 | 0 | 0 | 0 |
| Comp. Ex. B | 6 | 0.000 | 0.000 | −0.001 | −0.001 |
| Comp. Ex. B | 12 | 0.000 | 0.000 | −0.002 | −0.003 |
| Comp. Ex. B | 25 | 0.000 | −0.001 | −0.002 | −0.004 |
| Comp. Ex. B | 50 | −0.001 | −0.003 | −0.002 | −0.004 |
| Comp. Ex. B | 100 | −0.001 | −0.002 | −0.003 | −0.004 |
| Comp. Ex. B | 200 | −0.001 | −0.003 | −0.003 | −0.007 |
| Comp. Ex. B | 400 | −0.003 | −0.004 | −0.004 | −0.008 |
| Comp. Ex. A | 0 | 0 | 0 | 0 | 0 |
| Comp. Ex. A | 6 | −0.003 | −0.005 | −0.003 | −0.004 |
| Comp. Ex. A | 12 | −0.006 | −0.008 | −0.006 | −0.007 |
| Comp. Ex. A | 25 | −0.009 | −0.014 | −0.009 | −0.015 |
| Comp. Ex. A | 50 | −0.011 | −0.017 | −0.012 | −0.014 |
| Comp. Ex. A | 100 | −0.014 | −0.021 | −0.013 | −0.022 |
| Comp. Ex. A | 200 | −0.016 | −0.023 | −0.015 | −0.023 |
| Comp. Ex. A | 400 | −0.018 | −0.025 | −0.017 | −0.024 |

The response time of the sensor, $T_{90}$, is defined as the time for the change in response of the sensor to reach 90 percent of its final value after the methyl ethyl ketone (MEK) concentration was changed from 200 to 400 ppm. The capacitance $C_{90}$ is defined as $C_{90}$=((maximum capacitance at 400 ppm MEK−maximum capacitance at 200 ppm MEK)*0.9)+maximum capacitance at 200 ppm MEK $T_{90}$ is equal to the first time after the MEK concentration was changed from 200 ppm to 400 ppm when the capacitance reached the value of $C_{90}$.

The response time was determined from the $\Delta C/C_O$ data and is reported in Table 4.

TABLE 4

| SENSOR ELEMENT | Replicate $T_{90}$, sec | | | |
|---|---|---|---|---|
| | A | B | C | D |
| EXAMPLE 1 | 77 | 55 | 46 | 46 |
| EXAMPLE 2 | 47 | 47 | 45 | 42 |
| COMP. EX. C | 52 | 54 | 43 | 45 |
| COMP. EX. B | n/a | n/a | n/a | n/a |
| COMP. EX. A | n/a | n/a | n/a | n/a |

Comparative Examples D-F

Bottom electrodes were prepared as described in Example 1 using the SABE mask and were spin coated with PIMS as described in Example 1. The PIMS coated electrodes were sputtered coated with gold using the mask shown in FIG. 4 and then the samples were then vapor coated using the mask shown in FIG. 5 as in Example 1. The samples were then diced into individual sensor elements and tested for electrical shorts and base capacitance as described in Example 1. The sensor elements were stored as in Example 1 prior to testing. The description of the sensor elements produced is reported in Table 5 (below).

TABLE 5

| SENSOR ELEMENT | MEASURED PIMS THICKNESS, nm | SPUTTERED GOLD THICKNESS, nm |
|---|---|---|
| COMP. EX. D | 613 | 7.7 |
| COMP. EX. E | 602 | 10.0 |
| COMP. EX. F | 582 | 12.0 |

Comparative Examples D-F (six replicates of each) had a capacitance of about 1.7 nF as determined from the Protek multimeter, except that some of the Comparative Example F replicates shorted out. Dissipation factors and initial capacitance were measured with an Agilent LCR meter as described in Example 1 and are reported in Table 6 (below).

TABLE 6

|  | REPLICATE | | | |
| --- | --- | --- | --- | --- |
|  | A | B | C | D |
| COMP. EX. D | | | | |
| Initial Capacitance, pF | 1358.8 | 1294.6 | 1351.5 | 1363.2 |
| Initial Dissipation Factor | 0.006 | 0.002 | 0.002 | 0.003 |
| COMP. EX. E | | | | |
| Initial Capacitance, pF | 1244.2 | 1255.1 | 1261.3 | 1221.7 |
| Initial Dissipation Factor | 0.002 | 0.002 | 0.002 | 0.002 |
| COMP. EX. F | | | | |
| Initial Capacitance, pF | 1344.5 | 1341.1 | 1330.8 | 1335.6 |
| Initial Dissipation Factor | 0.001 | 0.001 | 0.002 | 0.001 |

The sensor elements were then tested for their response to MEK vapors using the same procedure as described in Example 1. They were not heated prior to vapor testing. The MEK vapor responses are reported in Table 7 (below).

TABLE 7

| EXAMPLE | MEK CONCENTRATION, ppm | REPLICATE, $\Delta C/C_O$ | | | |
| --- | --- | --- | --- | --- | --- |
|  |  | A | B | C | D |
| Comp. Ex. D | 0 | 0.000 | 0.000 | 0.000 | 0.000 |
| Comp. Ex. D | 6 | 0.002 | 0.003 | 0.000 | 0.002 |
| Comp. Ex. D | 12 | 0.004 | 0.006 | 0.000 | 0.003 |
| Comp. Ex. D | 25 | 0.006 | 0.010 | 0.001 | 0.006 |
| Comp. Ex. D | 50 | 0.010 | 0.016 | 0.002 | 0.009 |
| Comp. Ex. D | 100 | 0.014 | 0.022 | 0.003 | 0.013 |
| Comp. Ex. D | 200 | 0.020 | 0.031 | 0.006 | 0.019 |
| Comp. Ex. D | 400 | 0.027 | 0.040 | 0.010 | 0.026 |
| Comp. Ex. E | 0 | 0.000 | 0.000 | 0.000 | 0.000 |
| Comp. Ex. E | 6 | 0.003 | 0.001 | 0.003 | 0.001 |
| Comp. Ex. E | 12 | 0.007 | 0.003 | 0.006 | 0.003 |
| Comp. Ex. E | 25 | 0.011 | 0.004 | 0.009 | 0.005 |
| Comp. Ex. E | 50 | 0.016 | 0.007 | 0.013 | 0.008 |
| Comp. Ex. E | 100 | 0.022 | 0.010 | 0.018 | 0.012 |
| Comp. Ex. E | 200 | 0.029 | 0.014 | 0.024 | 0.017 |
| Comp. Ex. E | 400 | 0.036 | 0.019 | 0.030 | 0.022 |
| Comp. Ex. F | 0 | 0.000 | 0.000 | 0.000 | 0.000 |
| Comp. Ex. F | 6 | 0.002 | 0.002 | 0.003 | 0.002 |
| Comp. Ex. F | 12 | 0.002 | 0.003 | 0.004 | 0.003 |
| Comp. Ex. F | 25 | 0.004 | 0.005 | 0.006 | 0.004 |
| Comp. Ex. F | 50 | 0.006 | 0.007 | 0.009 | 0.006 |
| Comp. Ex. F | 100 | 0.008 | 0.010 | 0.012 | 0.009 |
| Comp. Ex. F | 200 | 0.012 | 0.013 | 0.017 | 0.012 |
| Comp. Ex. F | 400 | 0.016 | 0.017 | 0.022 | 0.016 |

The response time of the sensor, $T_{90}$, was determined from the $\Delta C/C_O$ data and is reported in Table 8 (below).

TABLE 8

| SENSOR | Replicate $T_{90}$, sec | | | |
| --- | --- | --- | --- | --- |
| ELEMENT | 1A | 1B | 1C | 1D |
| COMP. EX. D | 249 | 242 | 260 | 249 |
| COMP. EX. E | 232 | 245 | 250 | 247 |
| COMP. EX. F | 244 | 246 | 244 | 255 |

Effect of Heating on Sensor Element Response

Selected sensor elements prepared and tested in Examples 1 and 2 and Comparative Examples D, E, and F were heated to 150° C. for 1 hour, and then tested for their response to MEK vapor as described in Example 1. The initial capacitance and dissipation factors are reported in Table 9 (below).

TABLE 9

| EXAMPLE | 2 | – | – |
| --- | --- | --- | --- |
| Initial Capacitance, pF | 1200.3 | – | – |
| Initial Dissipation Factor | 0.0007 | – | – |
| EXAMPLE | 1 | – | – |
| Initial Capacitance, pF | 1225.8 | – | – |
| Initial Dissipation Factor | 0.0009 | – | – |
| COMPARATIVE EXAMPLE | D | E | F |
| Initial Capacitance, pF | 1321.2 | 1232.6 | 1274.6 |
| Initial Dissipation Factor | 0.0004 | 0.0004 | 0.0004 |

The $\Delta C/C_o$ responses to MEK vapor are reported in Table 10 (below).

TABLE 10

| MEK CONCENTRATION, ppm | $\Delta C/C_O$ | | | | |
| --- | --- | --- | --- | --- | --- |
|  | EXAMPLE 2 | EXAMPLE 1 | COMP. EX. D | COMP. EX. E | COMP. EX. F |
| 0 | 0.000 | 0.000 | 0.000 | 0.000 | 0.000 |
| 6 | 0.067 | 0.060 | 0.004 | 0.008 | 0.013 |
| 12 | 0.120 | 0.124 | 0.006 | 0.013 | 0.021 |
| 25 | 0.176 | 0.184 | 0.010 | 0.019 | 0.031 |
| 50 | 0.231 | 0.243 | 0.013 | 0.026 | 0.041 |
| 100 | 0.292 | 0.306 | 0.018 | 0.035 | 0.055 |
| 200 | 0.352 | 0.365 | 0.023 | 0.045 | 0.071 |
| 400 | 0.407 | 0.423 | 0.028 | 0.057 | 0.088 |

The response time of the sensor elements, $T_{90}$, was determined from the $\Delta C/C_O$ data and is reported in Table 11.

TABLE 11

| | REPLICATE, $T_{90}$, sec | | | |
|---|---|---|---|---|
| EXAMPLE 2 | EXAMPLE 1 | COMP. EX. D | COMP. EX. E | COMP. EX. F |
| 53 | 58 | 231 | 233 | 229 |

Examples 3-8 and Comparative Examples G-H

Sensor elements were prepared and stored before testing as described in Example 1. The description of the sensor elements is reported in Table 12. After dicing the samples into separate sensor elements, a Protek multimeter was used to test for shorts and measure a baseline capacitance. Sensor element specimens according to Examples 3 and 4 had a baseline capacitance of about 1.5 nF. Sensor element specimens according to Example 5 and Comparative Example G had a baseline capacitance of about 1.7 nF, and one specimen according to Comparative Example G shorted. Sensor element specimens according to Examples 6-8 and Comparative Example H had a baseline capacitance of about 1.6 nF, except for some specimens of Examples 6 and 8, and Comparative Example H, which shorted.

TABLE 12

| EXAMPLE | PIMS THICKNESS, nm | GOLD ELECTRODE THICKNESS, nm | GOLD ELECTRODE DEPOSITION RATE, nm/sec |
|---|---|---|---|
| 3 | 644 | 5.0 | 0.1 |
| 4 | 658 | 7.5 | 0.1 |
| 5 | 653 | 9.0 | 0.1 |
| Comp. Ex. G | 619 | 11.0 | 0.1 |
| 6 | 636 | 5.0 | 0.5 |
| 7 | 618 | 7.5 | 0.5 |
| 8 | 652 | 9.0 | 0.5 |
| Comp. Ex. H | 648 | 11.0 | 0.5 |

The sensor elements were tested for their response to MEK vapor as in Example 1. The sensor elements were not heated before the vapor test. The Initial Capacitance and Dissipation Factors were recorded after the sensor elements had been in the dry air of the testing chamber for about 5 to 10 minutes. These values are reported in Table 13 (below).

TABLE 13

| | REPLICATE | | | |
|---|---|---|---|---|
| | A | B | C | D |
| EXAMPLE 3 | | | | |
| Initial Capacitance, pF | 1180.7 | 993.9 | 1180.8 | 1204.5 |
| Initial Dissipation Factor | 0.0021 | 0.0017 | 0.0017 | 0.0113 |
| EXAMPLE 4 | | | | |
| Initial Capacitance, pF | 1149.7 | 1141.9 | 1154.6 | 1138.4 |
| Initial Dissipation Factor | 0.0014 | 0.0012 | 0.0040 | 0.0009 |
| EXAMPLE 5 | | | | |
| Initial Capacitance, pF | 1215.4 | 1194.8 | 1249.8 | 1201.4 |
| Initial Dissipation Factor | 0.0013 | 0.0012 | 0.0016 | 0.0010 |
| COMP. EX. G | | | | |
| Initial Capacitance, pF | 1216.7 | 1221.3 | 1206.1 | 1192.8 |
| Initial Dissipation Factor | 0.0011 | 0.0013 | 0.0013 | 0.0012 |
| EXAMPLE 6 | | | | |
| Initial Capacitance, pF | 1245.5 | 1208.9 | 1219.2 | 1201.4 |
| Initial Dissipation Factor | 0.0022 | 0.0013 | 0.0017 | 0.0014 |
| EXAMPLE 7 | | | | |
| Initial Capacitance, pF | 1190.2 | 1172.4 | 1197.7 | 1183.2 |
| Initial Dissipation Factor | 0.0011 | 0.0013 | 0.0196 | 0.0013 |
| EXAMPLE 8 | | | | |
| Initial Capacitance, pF | 1136.4 | 1151.9 | 1134.7 | 1132.6 |
| Initial Dissipation Factor | 0.0012 | 0.0011 | 0.0010 | 0.0010 |
| COMP. EX. H | | | | |
| Initial Capacitance, pF | 1164.5 | 1125.2 | 1191.4 | 1188.8 |
| Initial Dissipation Factor | 0.0011 | 0.0009 | 0.0011 | 0.0012 |

The response of the sensor elements to the various MEK vapor concentrations was recorded as a function of time. The final value at the end of 5 minutes at each concentration is reported in Table 14 (below).

TABLE 14

| EXAMPLE | MEK CONCENTRATION, ppm | REPLICATE, $\Delta C/C_0$ | | | |
|---|---|---|---|---|---|
| | | A | B | C | D |
| 3 | 0 | 0.000 | 0.000 | 0.000 | 0.000 |
| | 6 | 0.106 | 0.097 | 0.085 | 0.085 |
| | 12 | 0.149 | 0.144 | 0.139 | 0.134 |
| | 25 | 0.209 | 0.208 | 0.203 | 0.195 |
| | 50 | 0.269 | 0.272 | 0.265 | 0.258 |
| | 100 | 0.334 | 0.340 | 0.330 | 0.325 |
| | 200 | 0.397 | 0.406 | 0.393 | 0.390 |
| | 400 | 0.458 | 0.469 | 0.453 | 0.453 |
| 4 | 0 | 0.000 | 0.000 | 0.000 | 0.000 |
| | 6 | 0.095 | 0.107 | 0.099 | 0.098 |
| | 12 | 0.142 | 0.156 | 0.147 | 0.145 |
| | 25 | 0.196 | 0.211 | 0.202 | 0.199 |
| | 50 | 0.264 | 0.279 | 0.270 | 0.266 |
| | 100 | 0.333 | 0.347 | 0.338 | 0.333 |
| | 200 | 0.403 | 0.413 | 0.407 | 0.401 |
| | 400 | 0.468 | 0.477 | 0.473 | 0.466 |
| 5 | 0 | 0.000 | 0.000 | 0.000 | 0.000 |
| | 6 | 0.095 | 0.106 | 0.018 | 0.088 |
| | 12 | 0.143 | 0.152 | 0.033 | 0.135 |
| | 25 | 0.203 | 0.212 | 0.054 | 0.196 |
| | 50 | 0.268 | 0.277 | 0.080 | 0.262 |
| | 100 | 0.336 | 0.344 | 0.112 | 0.332 |
| | 200 | 0.404 | 0.411 | 0.151 | 0.402 |
| | 400 | 0.469 | 0.473 | 0.198 | 0.467 |
| COMP. EX. G | 0 | 0.000 | 0.000 | 0.000 | 0.000 |
| | 6 | 0.001 | 0.001 | 0.001 | 0.001 |
| | 12 | 0.002 | 0.002 | 0.002 | 0.002 |
| | 25 | 0.004 | 0.003 | 0.003 | 0.003 |
| | 50 | 0.006 | 0.004 | 0.004 | 0.004 |
| | 100 | 0.010 | 0.006 | 0.006 | 0.007 |
| | 200 | 0.015 | 0.009 | 0.009 | 0.010 |
| | 400 | 0.022 | 0.013 | 0.013 | 0.015 |
| 6 | 0 | 0.000 | 0.000 | 0.000 | 0.000 |
| | 6 | 0.095 | 0.103 | 0.100 | 0.102 |
| | 12 | 0.135 | 0.146 | 0.142 | 0.143 |
| | 25 | 0.193 | 0.207 | 0.203 | 0.204 |
| | 50 | 0.251 | 0.268 | 0.263 | 0.263 |
| | 100 | 0.318 | 0.336 | 0.331 | 0.330 |
| | 200 | 0.382 | 0.401 | 0.396 | 0.395 |
| | 400 | 0.444 | 0.463 | 0.458 | 0.458 |
| 7 | 0 | 0.000 | 0.000 | 0.000 | 0.000 |
| | 6 | 0.031 | 0.099 | 0.040 | 0.016 |
| | 12 | 0.067 | 0.149 | 0.080 | 0.044 |
| | 25 | 0.111 | 0.208 | 0.128 | 0.087 |
| | 50 | 0.167 | 0.273 | 0.187 | 0.148 |

TABLE 14-continued

| EXAMPLE | MEK CONCEN-TRATION, ppm | REPLICATE, ΔC/C$_O$ | | | |
|---|---|---|---|---|---|
| | | A | B | C | D |
| | 100 | 0.234 | 0.341 | 0.256 | 0.228 |
| | 200 | 0.309 | 0.408 | 0.333 | 0.319 |
| | 400 | 0.391 | 0.472 | 0.416 | 0.410 |
| 8 | 0 | 0.000 | 0.000 | 0.000 | 0.000 |
| | 6 | 0.002 | 0.001 | 0.001 | 0.001 |
| | 12 | 0.004 | 0.002 | 0.002 | 0.002 |
| | 25 | 0.008 | 0.003 | 0.004 | 0.003 |
| | 50 | 0.015 | 0.005 | 0.006 | 0.005 |
| | 100 | 0.025 | 0.008 | 0.011 | 0.009 |
| | 200 | 0.041 | 0.012 | 0.019 | 0.014 |
| | 400 | 0.068 | 0.019 | 0.032 | 0.023 |
| COMP. EX. H | 0 | 0.000 | 0.000 | 0.000 | 0.000 |
| | 6 | 0.001 | 0.001 | 0.001 | 0.001 |
| | 12 | 0.001 | 0.001 | 0.001 | 0.001 |
| | 25 | 0.002 | 0.001 | 0.002 | 0.002 |
| | 50 | 0.003 | 0.002 | 0.004 | 0.004 |
| | 100 | 0.005 | 0.004 | 0.005 | 0.005 |
| | 200 | 0.007 | 0.006 | 0.008 | 0.008 |
| | 400 | 0.009 | 0.009 | 0.011 | 0.011 |

The response time of the sensor elements, $T_{90}$, is reported in Table 15 (below).

TABLE 15

| EXAMPLE | REPLICATE $T_{90}$, sec | | | |
|---|---|---|---|---|
| | A | B | C | D |
| 3 | 48 | 69 | 60 | 71 |
| 4 | 71 | 42 | 69 | 53 |
| 5 | 60 | 58 | 247 | 77 |
| COMP. EX. G | 264 | 264 | 264 | 264 |
| 6 | 34 | 34 | 34 | 34 |
| 7 | 125 | 32 | 218 | 218 |
| 8 | 268 | 266 | 268 | 266 |
| COMP. EX. H | 258 | 258 | 256 | 261 |

Examples 9-12 and Comparative Example I-J

Figure 5:
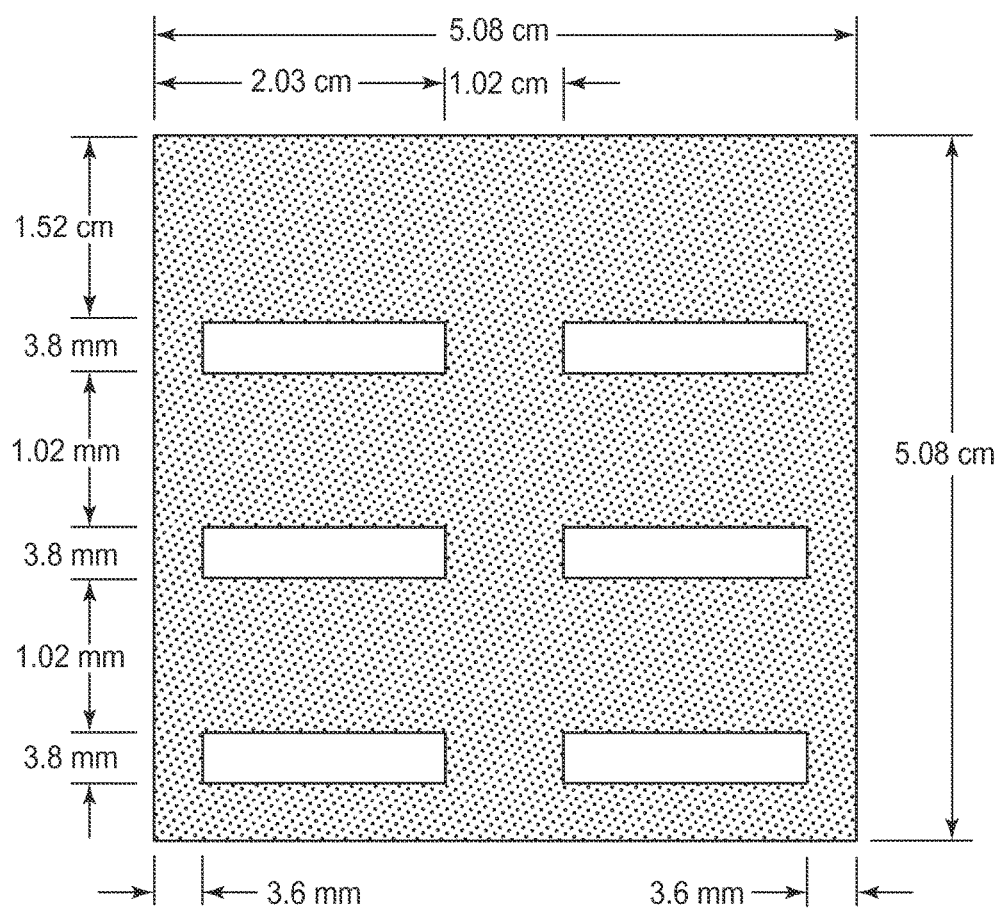

Sensor elements were prepared and stored before testing as described in Example 1, except that the top connecting electrode was deposited by thermal vapor coating 10.0 nm of titanium at a rate of 0.1 nm/sec followed by depositing 100.0 nm of nickel at 0.5 nm/sec through the mask shown in FIG. 5.

The description of the sensor elements is reported in Table 16. After dicing the samples into separate sensor elements, a Protek multimeter was used to test for shorts and measure a baseline capacitance. Comparative Examples I-J were not shorted, but did not function as capacitors. Example 9 had a baseline capacitance of about 1 nF, and one replicate shorted. Examples 10-11 had a baseline capacitance of about 1.7 nF.

TABLE 16

| EXAMPLE | PIMS THICKNESS, nm | GOLD ELECTRODE THICKNESS, nm | GOLD ELECTRODE DEPOSITION RATE, nm/sec |
|---|---|---|---|
| COMP. EX. I | 624 | 3.0 | 0.01 |
| 9 | 601 | 6.0 | 0.01 |
| 10 | 586 | 9.0 | 0.01 |

TABLE 16-continued

| EXAMPLE | PIMS THICKNESS, nm | GOLD ELECTRODE THICKNESS, nm | GOLD ELECTRODE DEPOSITION RATE, nm/sec |
|---|---|---|---|
| COMP. EX. J | 594 | 3.0 | 1.0 |
| 11 | 600 | 6.0 | 1.0 |
| 12 | 622 | 9.0 | 1.0 |

The sensor elements were tested for their response to MEK vapor as in Example 1. The sensor elements were not heated before the vapor test. The initial capacitance and dissipation factors were recorded after the sensor elements had been in the dry air of the testing chamber for about 5 to 10 minutes. These values are reported in Table 26.

TABLE 17

| | REPLICATE | | | |
|---|---|---|---|---|
| | A | B | C | D |
| COMP. EX. I | | | | |
| Initial Capacitance, pF | 1.4 | 1.0 | 1.4 | 0.8 |
| Initial Dissipation Factor | 0.2238 | 0.2195 | 0.1856 | 0.2299 |
| EXAMPLE 9 | | | | |
| Initial Capacitance, pF | 836.0 | 1150.5 | 1164.7 | 1249.3 |
| Initial Dissipation Factor | 7.6402 | 0.1720 | 0.1160 | 0.0094 |
| EXAMPLE 10 | | | | |
| Initial Capacitance, pF | 1241.5 | 1239.2 | 1249.8 | 1239.8 |
| Initial Dissipation Factor | 0.0011 | 0.0016 | 0.0013 | 0.0016 |
| COMP. EX. J | | | | |
| Initial Capacitance, pF | 1.3 | 0.8 | 1.2 | 0.9 |
| Initial Dissipation Factor | 2.4865 | 0.3350 | 0.2246 | 1.6910 |
| EXAMPLE 11 | | | | |
| Initial Capacitance, pF | 1252.0 | 1212.2 | 1238.9 | 1239.4 |
| Initial Dissipation Factor | 0.0012 | 0.0021 | 0.0013 | 0.0022 |
| EXAMPLE 12 | | | | |
| Initial Capacitance, pF | 1226.2 | 1241.8 | 1229.6 | 1240.0 |
| Initial Dissipation Factor | 0.0010 | 0.0011 | 0.0012 | 0.0010 |

The response of the sensor elements to the various MEK vapor concentrations was recorded as a function of time. The final value at the end of 5 minutes at each concentration is reported in Table 18 (below).

TABLE 18

| EXAMPLE | MEK CONCEN-TRATION, ppm | REPLICATE, ΔC/C$_O$ | | | |
|---|---|---|---|---|---|
| | | A | B | C | D |
| COMP. EX. I | 0 | 0.000 | 0.000 | 0.000 | 0.000 |
| | 6 | −0.001 | −0.002 | −0.001 | −0.004 |
| | 12 | −0.002 | −0.002 | −0.003 | −0.005 |
| | 25 | −0.004 | −0.005 | −0.004 | −0.008 |
| | 50 | −0.003 | −0.005 | −0.005 | −0.007 |
| | 100 | −0.005 | −0.007 | −0.006 | −0.010 |
| | 200 | −0.006 | −0.008 | −0.007 | −0.012 |
| | 400 | −0.007 | −0.009 | −0.008 | −0.012 |
| 9 | 0 | 0.000 | 0.000 | 0.000 | 0.000 |
| | 6 | 0.078 | 0.048 | 0.094 | 0.077 |
| | 12 | 0.141 | 0.109 | 0.141 | 0.124 |
| | 25 | 0.205 | 0.176 | 0.198 | 0.181 |
| | 50 | 0.270 | 0.235 | 0.258 | 0.243 |
| | 100 | 0.337 | 0.294 | 0.319 | 0.313 |
| | 200 | 0.401 | 0.349 | 0.378 | 0.386 |
| | 400 | 0.468 | 0.399 | 0.434 | 0.458 |

TABLE 18-continued

| EXAMPLE | MEK CONCENTRATION, ppm | REPLICATE, $\Delta C/C_O$ | | | |
|---|---|---|---|---|---|
| | | A | B | C | D |
| 10 | 0 | 0.000 | 0.000 | 0.000 | 0.000 |
| | 6 | 0.065 | 0.074 | 0.091 | 0.073 |
| | 12 | 0.133 | 0.133 | 0.140 | 0.138 |
| | 25 | 0.198 | 0.193 | 0.197 | 0.200 |
| | 50 | 0.261 | 0.256 | 0.259 | 0.262 |
| | 100 | 0.325 | 0.321 | 0.323 | 0.326 |
| | 200 | 0.389 | 0.386 | 0.388 | 0.392 |
| | 400 | 0.450 | 0.448 | 0.449 | 0.454 |
| COMP. EX. J | 0 | 0.000 | 0.000 | 0.000 | 0.000 |
| | 6 | 0.001 | 0.000 | −0.001 | −0.007 |
| | 12 | 0.000 | 0.000 | −0.002 | −0.007 |
| | 25 | 0.000 | −0.001 | −0.001 | −0.008 |
| | 50 | 0.000 | −0.004 | −0.002 | −0.010 |
| | 100 | 0.000 | −0.003 | −0.003 | −0.011 |
| | 200 | −0.001 | −0.004 | −0.004 | −0.013 |
| | 400 | −0.002 | −0.004 | −0.004 | −0.016 |
| 11 | 0 | 0.000 | 0.000 | 0.000 | 0.000 |
| | 6 | 0.080 | 0.088 | 0.097 | 0.091 |
| | 12 | 0.145 | 0.149 | 0.145 | 0.143 |
| | 25 | 0.207 | 0.210 | 0.202 | 0.202 |
| | 50 | 0.270 | 0.271 | 0.263 | 0.261 |
| | 100 | 0.335 | 0.337 | 0.328 | 0.326 |
| | 200 | 0.399 | 0.402 | 0.393 | 0.390 |
| | 400 | 0.459 | 0.462 | 0.452 | 0.449 |
| 12 | 0 | 0.000 | 0.000 | 0.000 | 0.000 |
| | 6 | 0.003 | 0.011 | 0.004 | 0.004 |
| | 12 | 0.010 | 0.033 | 0.012 | 0.012 |
| | 25 | 0.025 | 0.077 | 0.027 | 0.030 |
| | 50 | 0.051 | 0.145 | 0.054 | 0.060 |
| | 100 | 0.096 | 0.239 | 0.101 | 0.115 |
| | 200 | 0.172 | 0.346 | 0.181 | 0.208 |
| | 400 | 0.282 | 0.443 | 0.305 | 0.351 |

The response time of the sensor elements, $T_{90}$, is reported in Table 19. For sensor elements according to Comparative Examples I and J, the $T_{90}$ value could not be determined due to the poor response of the sensor element.

TABLE 19

| SENSOR ELEMENT | Replicate $T_{90}$, sec | | | |
|---|---|---|---|---|
| | A | B | C | D |
| COMP. EX. I | n/a | n/a | n/a | n/a |
| EXAMPLE 9 | 142.3 | 126.8 | 102.0 | 177.0 |
| EXAMPLE 10 | 111.4 | 111.4 | 99.6 | 99.6 |
| COMP. EX. J | n/a | n/a | n/a | n/a |
| EXAMPLE 11 | 144.8 | 142.6 | 133.8 | 140.3 |
| EXAMPLE 12 | 261.6 | 226.5 | 263.7 | 261.6 |

Examples 13-16 and Comparative Examples K-L

The sensor elements of EXAMPLES 9-12 and COMPARATIVE EXAMPLE I-J were also tested for their response to MEK vapor as described in Example 1, except that the sensor elements were heated for 1 hour at 150° C. before the vapor tests resulting in, respectively, EXAMPLES 13-16 and COMPARATIVE EXAMPLES K-L.

The initial capacitance and dissipation factors were recorded after the sensor elements had been in the dry air of the testing chamber for about 5 to 10 minutes. This data is reported in Table 20. Example 9, Replicate A was damaged before the test and that produced both a lower capacitance and higher dissipation factor.

TABLE 20

| EXAMPLE | | REPLICATE | |
|---|---|---|---|
| | | A | B |
| COMP. EX. K | Initial Capacitance, pF | 1.381 | 1.082 |
| | Initial Dissipation Factor | −0.0028 | 0.0065 |
| 13 | Initial Capacitance, pF | 148.4 | 1232.3 |
| | Initial Dissipation Factor | 0.0564 | 0.0042 |
| 14 | Initial Capacitance, pF | 1252.2 | 1243.8 |
| | Initial Dissipation Factor | 0.0005 | 0.0010 |
| COMP. EX. L | Initial Capacitance, pF | 1.211 | 0.836 |
| | Initial Dissipation Factor | −0.0105 | −0.0027 |
| 15 | Initial Capacitance, pF | 1235.2 | 1231.7 |
| | Initial Dissipation Factor | 0.0005 | 0.0005 |
| 16 | Initial Capacitance, pF | 1232.2 | 1245.1 |
| | Initial Dissipation Factor | 0.0004 | 0.0004 |

The response of the sensor elements to the various MEK vapor concentrations was recorded as a function of time. The final value at the end of 5 minutes at each concentration is reported in Table 21 (below).

TABLE 21

| EXAMPLE | MEK CONCENTRATION, ppm | REPLICATE, $\Delta C/C_O$ | |
|---|---|---|---|
| | | A | B |
| COMP. EX. K | 0 | 0.000 | 0.000 |
| | 6 | 0.004 | −0.001 |
| | 12 | −0.002 | −0.002 |
| | 25 | −0.001 | −0.004 |
| | 50 | −0.004 | −0.004 |
| | 100 | −0.006 | −0.007 |
| | 200 | −0.006 | −0.007 |
| | 400 | −0.007 | −0.009 |
| 13 | 0 | 0.000 | 0.000 |
| | 6 | 0.081 | 0.090 |
| | 12 | 0.121 | 0.131 |
| | 25 | 0.171 | 0.185 |
| | 50 | 0.224 | 0.243 |
| | 100 | 0.281 | 0.306 |
| | 200 | 0.336 | 0.367 |
| | 400 | 0.391 | 0.426 |
| 14 | 0 | 0.000 | 0.000 |
| | 6 | 0.090 | 0.093 |
| | 12 | 0.135 | 0.136 |
| | 25 | 0.186 | 0.185 |
| | 50 | 0.244 | 0.245 |
| | 100 | 0.306 | 0.308 |
| | 200 | 0.369 | 0.372 |
| | 400 | 0.429 | 0.432 |
| COMP. EX. L | 0 | 0.000 | 0.000 |
| | 6 | 0.000 | −0.001 |
| | 12 | −0.001 | −0.001 |
| | 25 | −0.001 | −0.003 |
| | 50 | −0.003 | −0.004 |
| | 100 | 0.000 | −0.005 |
| | 200 | −0.005 | −0.006 |
| | 400 | −0.005 | −0.009 |
| 15 | 0 | 0.000 | 0.000 |
| | 6 | 0.088 | 0.091 |
| | 12 | 0.128 | 0.128 |
| | 25 | 0.187 | 0.188 |
| | 50 | 0.246 | 0.247 |
| | 100 | 0.308 | 0.309 |
| | 200 | 0.371 | 0.372 |
| | 400 | 0.421 | 0.432 |
| 16 | 0 | 0.000 | 0.000 |
| | 6 | 0.076 | 0.070 |
| | 12 | 0.124 | 0.125 |
| | 25 | 0.184 | 0.188 |
| | 50 | 0.244 | 0.249 |
| | 100 | 0.307 | 0.312 |
| | 200 | 0.370 | 0.375 |
| | 400 | 0.431 | 0.436 |

The response time of the sensor elements, $T_{90}$, is reported in Table 22 (below)

TABLE 22

| EXAMPLE | Replicate $T_{90}$, sec | |
|---|---|---|
| | A | B |
| COMP. EX. K | n/a | n/a |
| 13 | 101 | 94 |
| 14 | 98 | 96 |
| COMP. EX. L | n/a | n/a |
| 15 | 93 | 95 |
| 16 | 104 | 95 |

Examples 17-18

Sensor elements were prepared according to the procedure described in Example 1, except that palladium (6.0 nm thickness, deposited at a rate of 0.1 nm/sec) was used to prepare the top electrode instead of gold. Because of the high melting point of palladium (>1550° C.), e-beam heating was used instead of resistance heating, but the vacuum conditions were the same. The PIM layer thickness for this example was 600 nm.

After dicing, some of the replicate sensor elements were heated at 150° C. for one hour (Example 18) prior to testing, and some were not (Example 17). The resulting sensor elements were stored in sealed glass jars in the dark with 20 packets of an Activated Carbon/Silica Gel to protect them from unintended exposure to organic vapors or moisture. The sensor elements were stored in this manner until testing for organic vapor response.

The sensor elements were tested for their response to MEK vapor as in Example 1. The Initial Capacitance and Dissipation Factors were recorded after the sensor elements had been in the dry air of the testing chamber for about 5 to 10 minutes. These values are reported in Table 23 (below).

TABLE 23

| EXAMPLE | | REPLICATE, $\Delta C/C_O$ | |
|---|---|---|---|
| | | A | B |
| 17 | Initial Capacitance, pF | 1208.8 | 1200.4 |
| | Initial Dissipation Factor | 0.0020 | 0.0021 |
| 18 | Initial Capacitance, pF | 1210.8 | 1200.8 |
| | Initial Dissipation Factor | 0.0014 | 0.0015 |

The response of the palladium conductive electrode-containing sensor elements to various MEK vapor concentrations was recorded as a function of time. The final $\Delta C/C_o$ value at the end of 5 minutes at each concentration is reported in Table 24 (below).

TABLE 24

| EXAMPLE | MEK CONCENTRATION, ppm | REPLICATE, $\Delta C/C_O$ | |
|---|---|---|---|
| | | A | B |
| 17 | 0 | 0 | 0 |
| | 6 | 0.038 | 0.052 |
| | 12 | 0.094 | 0.106 |
| | 25 | 0.149 | 0.153 |
| | 50 | 0.211 | 0.212 |
| | 100 | 0.279 | 0.277 |
| | 200 | 0.348 | 0.346 |
| | 400 | 0.417 | 0.415 |
| 18 | 0 | 0 | 0 |
| | 6 | 0.036 | 0.056 |
| | 12 | 0.087 | 0.100 |
| | 25 | 0.138 | 0.142 |
| | 50 | 0.196 | 0.197 |
| | 100 | 0.260 | 0.257 |
| | 200 | 0.326 | 0.323 |
| | 400 | 0.393 | 0.389 |

The response time of the sensor elements, $T_{90}$, is reported in Table 25 (below)

TABLE 25

| | Replicate $T_{90}$, sec | |
|---|---|---|
| | A | B |
| EXAMPLE 17 | 68.6 | 51.0 |
| EXAMPLE 18 | 59.9 | 41.8 |

Examples 19-22

Sensor elements were prepared according to the procedure described in Example 1, except that platinum (5.0 nm and 7.0 nm thickness, deposited at a rate of 0.1 nm/sec) was used to prepare the top electrode instead of gold. Because of the vapor deposition characteristics of platinum (1768.3° C.), e-beam heating was used instead of resistance heating, but the vacuum conditions were the same. For the 5.0 nm platinum top electrode examples (Examples 19-20), the polymer thickness was 600 nm. For the 7.0 nm platinum top electrode examples (Examples 21-22), the polymer thickness was 605 nm.

After dicing, some of the replicate sensor elements were heated at 150° C. for one hour prior to testing, and some were not. The resulting sensor elements were stored in sealed glass jars in the dark with 30 packets of an Activated Carbon/Silica Gel to protect them from unintended exposure to organic vapors or moisture. The sensor elements were stored in this manner until testing for organic vapor response.

The sensor elements were tested for their response to MEK vapor as in Example 1. The Initial Capacitance and Dissipation Factors were recorded after the sensor elements had been in the dry air of the testing chamber for about 5 to 10 minutes. These values are reported in Table 26 (below).

TABLE 26

| EXAMPLE | PLATINUM ELECTRODE and THICKNESS | Initial Capacitance, pF | Initial Dissipation Factor |
|---|---|---|---|
| 19 | not heat-treated, 5.0 nm | 1208.8 | 0.0020 |
| 20 | heat-treated, 5.0 nm | 1228.1 | 0.0016 |
| 21 | not heat-treated, 7.0 nm | 1171.7 | 0.0013 |
| 22 | heat-treated, 7.0 nm | 1207.6 | 0.0015 |

The response of the sensor elements to various MEK vapor concentrations was recorded as a function of time. The final $\Delta C/C_o$ value at the end of 5 minutes at each concentration is reported in Table 27 (below).

TABLE 27

| EXAMPLE | MEK CONCENTRATION, ppm | $\Delta C/C_O$ |
|---|---|---|
| 19 | 0 | 0.000 |
|  | 6 | 0.003 |
|  | 12 | 0.007 |
|  | 25 | 0.015 |
|  | 50 | 0.028 |
|  | 100 | 0.049 |
|  | 200 | 0.081 |
|  | 400 | 0.131 |
| 20 | 0 | 0.000 |
|  | 6 | 0.071 |
|  | 12 | 0.130 |
|  | 25 | 0.193 |
|  | 50 | 0.254 |
|  | 100 | 0.319 |
|  | 200 | 0.386 |
|  | 400 | 0.449 |
| 21 | 0 | 0.000 |
|  | 6 | 0.001 |
|  | 12 | 0.002 |
|  | 25 | 0.003 |
|  | 50 | 0.005 |
|  | 100 | 0.008 |
|  | 200 | 0.012 |
|  | 400 | 0.018 |
| 22 | 0 | 0.000 |
|  | 6 | 0.032 |
|  | 12 | 0.067 |
|  | 25 | 0.114 |
|  | 50 | 0.172 |
|  | 100 | 0.244 |
|  | 200 | 0.326 |
|  | 400 | 0.411 |

The response time of the sensor elements, $T_{90}$, is reported in Table 28 (below)

TABLE 28

| EXAMPLE | $T_{90}$, sec |
|---|---|
| 19 | 268.7 |
| 20 | 88.5 |
| 21 | 264.2 |
| 22 | 236.0 |

All examples given herein are to be considered non-limiting unless otherwise indicated. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A sensor element comprising:
   a first conductive electrode having a first conductive member electrically coupled thereto;
   an absorptive dielectric layer comprising a polymer of intrinsic microporosity; and
   a second conductive electrode having a second conductive member electrically coupled thereto, wherein the second conductive electrode is coextensive with a major surface of the absorptive dielectric layer, and consists essentially of at least one noble metal, wherein the second conductive electrode has a thickness of from 4 to 9 nanometers and is permeable to at least one organic vapor, and wherein the absorptive dielectric layer is at least partially disposed between the first conductive electrode and the second conductive electrode such that the sensor element is configured to work as a capacitor and a capacitance of the sensor element is changeable upon absorption of the at least one organic vapor.

2. The sensor element of claim 1, further comprising a dielectric substrate supporting the first conductive electrode.

3. The sensor element of claim 2, wherein the dielectric substrate comprises a polymeric film.

4. The sensor element of claim 1, wherein the at least one noble metal comprises at least 99 percent by weight of the second conductive electrode.

5. The sensor element of claim 1, wherein the second conductive electrode comprises gold, palladium, platinum, or a combination thereof.

6. The sensor element of claim 1, wherein the polymer of intrinsic microporosity comprises organic macromolecules comprised of generally planar species connected by rigid linkers, said rigid linkers having a point of contortion such that two adjacent planar species connected by one of the rigid linkers are held in non-coplanar orientation.

7. The sensor element of claim 1, wherein the first conductive electrode comprises at least one noble metal, and wherein the first conductive electrode has a thickness of from 4 to 10 nanometers and is permeable to at least one organic vapor.

8. The sensor element of claim 1, wherein the second conductive electrode is thermal-vapor deposited onto a major surface of the absorptive dielectric layer.

9. A method comprising steps of:
   disposing an absorptive dielectric layer comprising a polymer of intrinsic microporosity on a first conductive electrode; and
   disposing by thermal vapor deposition a second conductive electrode onto a major surface of the absorptive dielectric layer, wherein the second conductive electrode has a thickness of from 4 to 9 nanometers after the thermal vapor deposition is complete, wherein the second conductive electrode includes at least one noble metal disposed by thermal vapor deposition that is permeable to at least one organic vapor, and wherein the absorptive dielectric layer is at least partially disposed between the first conductive electrode and the second conductive electrode such that the sensor element is configured to work as a capacitor and a capacitance of the sensor element is changeable upon absorption of the at least one organic vapor.

10. The method of claim 9, wherein the first conductive electrode is supported on a dielectric substrate.

11. The method of claim 10, wherein the dielectric substrate comprises a polymeric film.

12. The method of claim 9, wherein the steps are sequential.

13. The method of claim 9, wherein the at least one noble metal comprises at least 99 percent by weight of the second conductive electrode.

14. The method of claim 9, wherein the second conductive electrode comprises gold, palladium, platinum, or a combination thereof.

15. The method of claim 9, wherein the polymer of intrinsic microporosity comprises organic macromolecules comprised of generally planar species connected by rigid linkers, said rigid linkers having a point of contortion such that two adjacent planar species connected by the rigid linkers are held in non-coplanar orientation.

16. The method of claim 9, wherein the first conductive electrode comprises at least one noble metal, and wherein the first conductive electrode has a thickness of from 4 to 10 nanometers and is permeable to at least one organic vapor.

17. The method of claim 9, further comprising heating at least the second electrode at a temperature in a range of from 100 to 250 degrees Celsius.

18. A sensor device comprising:
   a sensor chamber having an inlet opening, a sensor element having a capacitance, disposed within the sensor chamber, and in fluid communication with the inlet opening, wherein the sensor element comprises:
      a first conductive electrode having a first conductive member electrically couple thereto;
      an absorptive dielectric layer comprising a polymer of intrinsic microporosity; and
      a second conductive electrode having a second conductive member electrically coupled thereto, wherein the second conductive electrode consists essentially of at least one noble metal, wherein the second conductive electrode has a thickness from 4 to 9 nanometers and is permeable to at least one organic vapor, and wherein the absorptive dielectric layer is at least partially disposed between the first conductive electrode and the second conductive electrode such that the sensor element is configured to work as a capacitor and the capacitance of the sensor element is changeable upon absorption of the at least one organic vapor;
   an operating circuit in electrical communication with the sensor element, whereby if the sensor element is connected to a source of electrical power, the operating circuit measures the capacitance of the sensor element.

19. The sensor device of claim 18, wherein the sensor chamber further comprises an outlet opening in fluid communication with the inlet opening.

20. The sensor device of claim 18, further comprising a display device communicatively coupled with the operating circuit.

21. The sensor device of claim 18, wherein the second conductive electrode comprises gold, palladium, platinum, or a combination thereof.

22. The sensor device of claim 18, wherein the second conductive electrode is thermal-vapor deposited onto a major surface of the absorptive dielectric layer.

* * * * *